(12) United States Patent
Grunewald Highsmith et al.

(10) Patent No.: US 12,161,391 B2
(45) Date of Patent: *Dec. 10, 2024

(54) CATHETER ADAPTED FOR DIRECT TISSUE CONTACT

(71) Applicant: BIOSENSE WEBSTER (ISRAEL) LTD., Yokneam (IL)

(72) Inventors: Debby Grunewald Highsmith, Laguna Nigel, CA (US); Meir Bar-Tal, Zikhron Ya'akov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 194 days.

This patent is subject to a terminal disclaimer.

(21) Appl. No.: 16/273,098

(22) Filed: Feb. 11, 2019

(65) Prior Publication Data

US 2019/0167347 A1 Jun. 6, 2019

Related U.S. Application Data

(63) Continuation of application No. 13/224,291, filed on Sep. 1, 2011, now Pat. No. 10,201,385.

(51) Int. Cl.
*A61B 18/14* (2006.01)
*A61B 18/00* (2006.01)

(52) U.S. Cl.
CPC ...... *A61B 18/1492* (2013.01); *A61B 18/1482* (2013.01); *A61B 2018/00029* (2013.01);
(Continued)

(58) Field of Classification Search
CPC ............ A61B 18/1477; A61B 18/1482; A61B 18/1492; A61B 2018/00797;
(Continued)

(56) References Cited

U.S. PATENT DOCUMENTS 5,366,443 A * 11/1994 Eggers ............... A61B 18/1492
604/114
5,383,874 A 1/1995 Jackson et al.
(Continued)

FOREIGN PATENT DOCUMENTS

CN 1211171 A 3/1999
CN 1895183 A 1/2007
(Continued)

OTHER PUBLICATIONS

English language translation of JPO Notification of Reasons for Refusal dated May 24, 2016 for JP Patent Application No. 2012-191328, 7 pages.
(Continued)

*Primary Examiner* — Pamela M. Bays
(74) *Attorney, Agent, or Firm* — Frost Brown Todd LLP

(57) ABSTRACT

An irrigated ablation catheter adapted for direct tissue contact has micro-elements that provide more accurate sensing of tissue, including thermal and electrical properties for temperature and impedance measurements. The micro-elements extend through a hollow chamber of an irrigated ablation electrode, and distal ends thereof can protrude outside of electrode or be flush with the electrode. The micro-elements have a protective guide tube in which components enabling temperature sensing or electrical sensing are encased.

20 Claims, 16 Drawing Sheets

(52) U.S. Cl.
CPC .............. *A61B 2018/00702* (2013.01); *A61B 2018/00797* (2013.01); *A61B 2018/00821* (2013.01); *A61B 2018/00839* (2013.01); *A61B 2018/00875* (2013.01); *A61B 18/1477* (2013.01); *A61B 2218/002* (2013.01)

(58) Field of Classification Search
CPC ........... A61B 2018/00875; A61B 2018/00702; A61B 2218/002
See application file for complete search history.

(56) References Cited

U.S. PATENT DOCUMENTS

| | | | |
|---|---|---|---|
| 5,458,597 | A | 10/1995 | Edwards et al. |
| 5,688,267 | A | 11/1997 | Panescu et al. |
| 5,755,715 | A | 5/1998 | Stern et al. |
| 5,853,409 | A | 12/1998 | Swanson et al. |
| 5,964,757 | A | 10/1999 | Ponzi |
| 6,030,379 | A | 2/2000 | Panescu et al. |
| 6,063,078 | A | 5/2000 | Wittkampf |
| 6,090,105 | A | 7/2000 | Zepeda et al. |
| 6,176,857 | B1 | 1/2001 | Ashley |
| 6,371,955 | B1 | 4/2002 | Fuimaono et al. |
| 6,425,887 | B1 | 7/2002 | Mcguckin et al. |
| 6,468,260 | B1 | 10/2002 | Bumbalough et al. |
| 6,500,167 | B1 | 12/2002 | Webster, Jr. |
| 6,500,172 | B1 | 12/2002 | Panescu et al. |
| 6,522,933 | B2 | 2/2003 | Nguyen |
| 6,611,699 | B2 | 8/2003 | Messing |
| 6,616,657 | B2 | 9/2003 | Simpson et al. |
| 6,638,275 | B1 | 10/2003 | McGaffigan et al. |
| 6,689,127 | B1 | 2/2004 | Gough et al. |
| 7,047,068 | B2 | 5/2006 | Haissaguerre |
| 7,094,215 | B2 | 8/2006 | Davison et al. |
| 8,792,962 | B2 | 7/2014 | Esguerra et al. |
| 8,900,228 | B2 | 12/2014 | Grunewald et al. |
| 2003/0004506 | A1 | 1/2003 | Messing |
| 2003/0109871 | A1 | 6/2003 | Johnson et al. |
| 2004/0092806 | A1* | 5/2004 | Sagon .................. A61B 5/0422 600/374 |
| 2007/0287998 | A1 | 12/2007 | Sharareh et al. |
| 2008/0140169 | A1 | 6/2008 | Imran |
| 2008/0243214 | A1* | 10/2008 | Koblish ............... A61B 5/6855 600/374 |
| 2009/0012592 | A1 | 1/2009 | Buysman |
| 2009/0138007 | A1 | 5/2009 | Govari et al. |
| 2009/0163916 | A1 | 6/2009 | Paul |
| 2010/0331658 | A1 | 12/2010 | Kim |
| 2011/0130648 | A1 | 6/2011 | Beeckler et al. |
| 2011/0224573 | A1 | 9/2011 | Bar-tal |
| 2011/0224667 | A1 | 9/2011 | Koblish et al. |
| 2012/0143088 | A1 | 6/2012 | Schultz |

FOREIGN PATENT DOCUMENTS

| | | |
|---|---|---|
| CN | 101780303 A | 7/2010 |
| CN | 102078187 A | 6/2011 |
| EP | 1922991 A1 | 5/2008 |
| EP | 2047797 A2 | 4/2009 |
| EP | 2062545 A2 | 5/2009 |
| EP | 2347726 A2 | 7/2011 |
| EP | 2564801 A1 | 3/2013 |
| EP | 2327365 B1 | 7/2013 |
| JP | 08-503381 A | 2/2008 |
| JP | 2010503959 A | 2/2010 |
| JP | 2011-115581 A | 6/2011 |
| JP | 2011-506947 A | 12/2011 |
| KR | 100243503 B | 12/1997 |
| WO | WO9308755 A1 | 5/1993 |
| WO | 1996036860 A2 | 11/1996 |
| WO | 9706739 A2 | 2/1997 |
| WO | WO9733524 A1 | 9/1997 |
| WO | WO9925260 A1 | 5/1999 |
| WO | WO2008118992 A1 | 10/2008 |
| WO | 2009082635 A1 | 7/2009 |
| WO | 2013166391 A1 | 11/2013 |

OTHER PUBLICATIONS

English translation of SIPO First Office Action dated Jun. 1, 2016 for CN Patent Application No. 201380023374.9, 4 pages.
English translation of SIPO Office action dated Sep. 14, 2015 in CN Application No. 201210320563.X, 3 pages.
Extended European Search Report dated Nov. 16, 2012 for EP Application No. 12182618.4, 6 pages.
International Search Report and Written Opinion of the International Searching Authority, dated Oct. 23, 2013, issued in PCT/US2013/039477, 8 pages.
International Search Report of the International Searching Authority, dated Nov. 4, 2014, for International application No. PCT/US2013/039477, 11 pages.
Written Opinion of the International Searching Authority, dated Oct. 23, 2013, for International application No. PCT/US2013/9477, 10 pages.
English translation of JPO Notification of Reasons for Refusal dated Mar. 30, 2017 for JP Patent Application No. 2015-510482, 4 pages.
English translation of JPO Notification of Reasons for Refusal dated May 19, 20167 for JP Patent Application No. 2012-191328, 7 pages.
EP Communication dated Jun. 16, 2019, for European Patent Application No. 13722948.0, 5 pages.
EP Communication dated Feb. 6, 2023, for European Patent Application No. 19182321, 5 pages.
Extended European Search Report dated Oct. 19, 2022, for European Patent Application No. 19182321, 7 pages.
Extended European Search Report dated Nov. 16, 2012, for European Patent Application No. 12182618.4, 6 pages.
English Translation of SIPO Third Office Action, dated Aug. 1, 2017, for China Patent Application No. 201380023374.9, 3 pages.
English Translation of SIPO Supplemental Search report, for China Application No. 201380023374.9. 3 pages.
English Translation of SIPO Second Office Action, dated Jan. 19, 2017, for China Patent Application No. 201380023374.9, 3 pages.
English Translation of SIPO Text of Second Office Action, dated Jan. 19, 2017, for China Patent Application No. 201380023374.9, 8 pages.
SIPO First Search, for China Patent Application No. 201380023374.9, 3 pages.
English Translation of SIPO First Office Action, dated Jun. 1, 2016, for China Patent Application No. 201380023374.9, 4 pages.
English Translation of SIPO Text of First Office Action, for China Patent Application No. 201380023374.9, 9 pages.
English Translation of SIPO Third Office Action, dated Sep. 30, 2006, for China Patent Application No. 201210320563.X, 3 pages.
English Translation of SIPO Second Office Action, dated May 23, 2016, for China Patent Application No. 201210320563.X, 3 pages.
English Translation of SIPO Text of Second Office Action, for China Patent Application No. 201210320563.X, 9 pages.
English Translation of SIPO Text of First Office Action, for China Patent Application No. 201210320563.X, 8 pages.
SIPO Text of First Search Report for China Patent Application No. 201210320563.x, 3 pages.
Canadian Office action for Application No. 2871921, 6 pages.
Canadian Office action for Application No. 2788138, 4 pages.
Australian Examination Report No. 4 for Patent Application No. 2012216328, dated Jan. 28, 2016, 4 pages.
Australian Examination Report No. 3 for Patent Application No. 2012216328, dated Jan. 13, 2016, 4 pages.
Australian Examination Report No. 2 for Patent Application No. 2012216328, dated Jul. 25, 2015, 3 pages.
Australian Examination Report No. 1 for Patent Application No. 2012216328, dated Apr. 30, 2014, 3 pages.
Australian Examination Report No. 1 for Patent Application No. 2018278889, dated Sep. 1, 2011, 5 pages.
Australian Examination Report No. 1 for Patent Application No. 2016200547, dated Sep. 1, 2011, 5 pages.

(56) References Cited

OTHER PUBLICATIONS

Written Opinion of the International Search Authority, dated Oct. 23, 2013, for International application No. PCT/ US/2013/039477, 10 pages.
English Translation of JPO Notification of Reasons for Refusal dated May 19, 2016 for JP Patent Application No. 2012-191328, 7 pages.
EP Communication dated Jul. 16, 2019, for European Patent Application No. 13722948.0, 5 pages.
Canadian Office action for Application No. 2871921, dated Feb. 19, 2019, 6 pages.
Canadian Office action for Application No. 2788138, dated Jun. 22, 2018, 4 pages.
Australian Examination Report No. 1 for Patent Application No. 2018278889, dated Aug. 16, 2019, 5 pages.
Australian Examination Report No. 1 for Patent Application No. 2016200547, dated Dec. 12, 2017, 5 pages.
SIPO First Search, for China Patent Application No. 201380023374.9, dated Jun. 1, 2016, 3 pages.
SIPO Supplementary Search Report for China Application No. 201380023374.9, dated Jan. 19, 2017, 3 pages.
English Translation of SIPO Text of Third Office action, dated Sep. 30, 2016, for China Patent Application No. 201210320563.X, 3 pages.
English Translation of SIPO Text of Third Office action, dated Aug. 1, 2017, for China Patent Application No. 201380023374.9, 3 pages.

\* cited by examiner

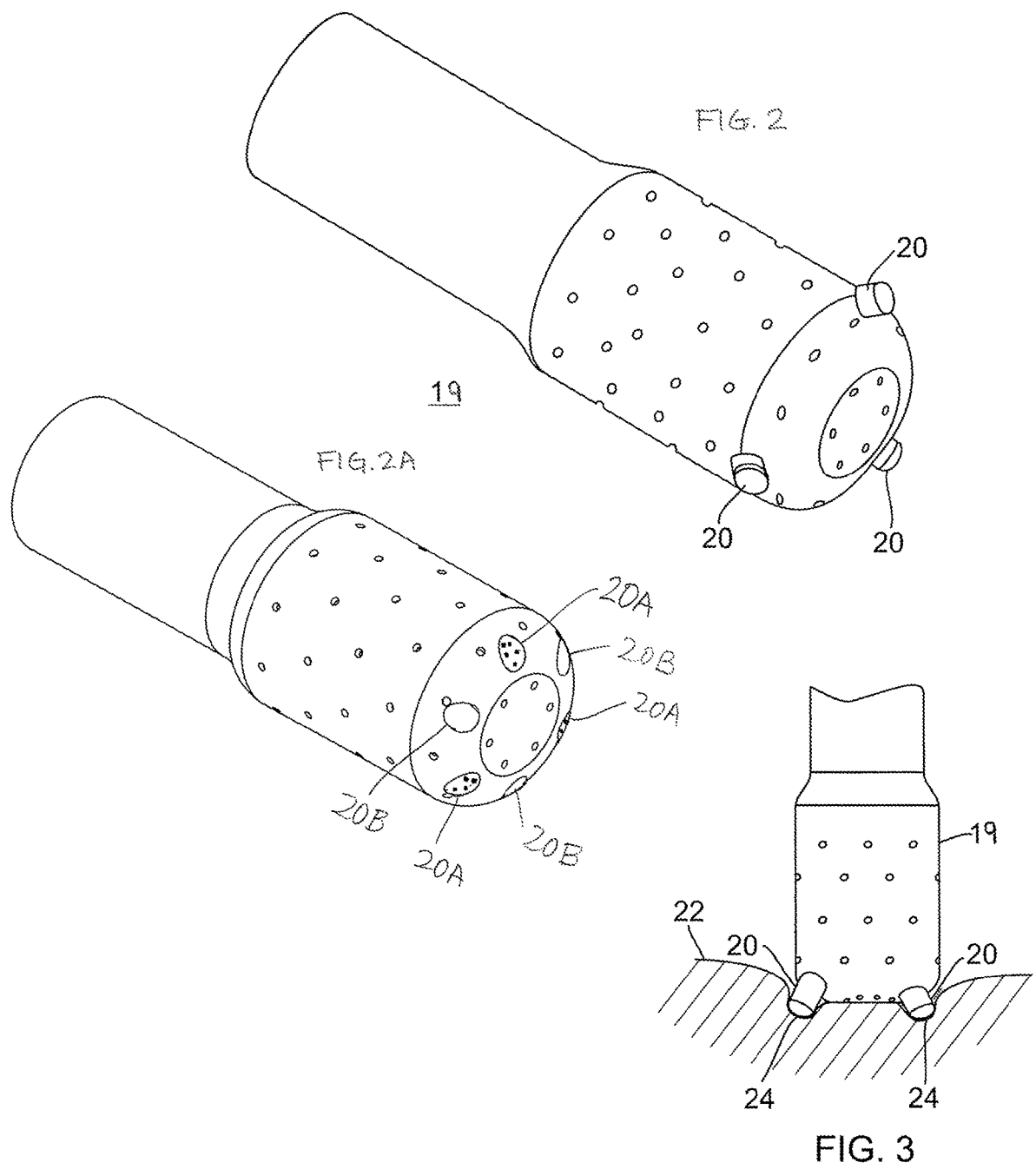

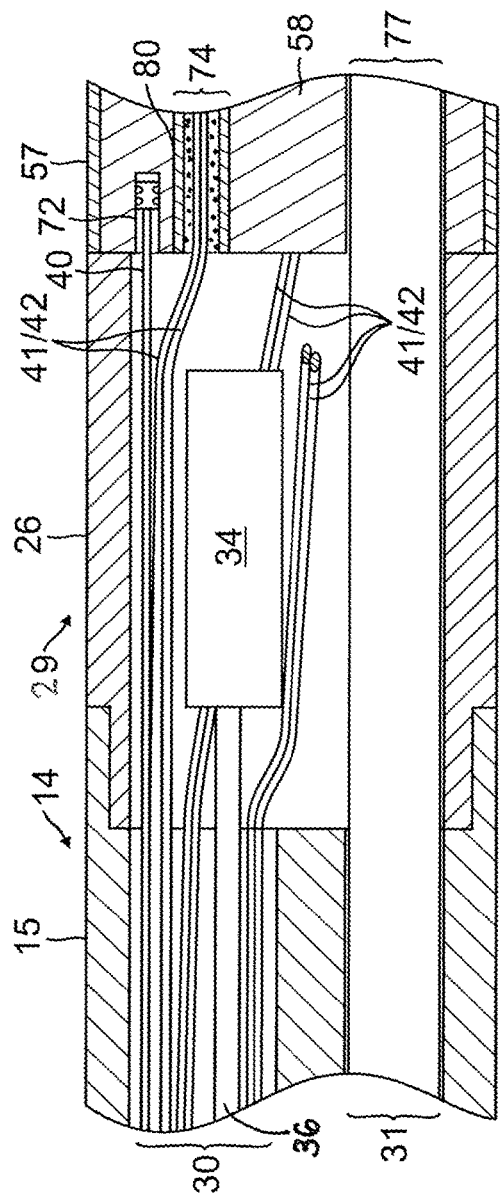
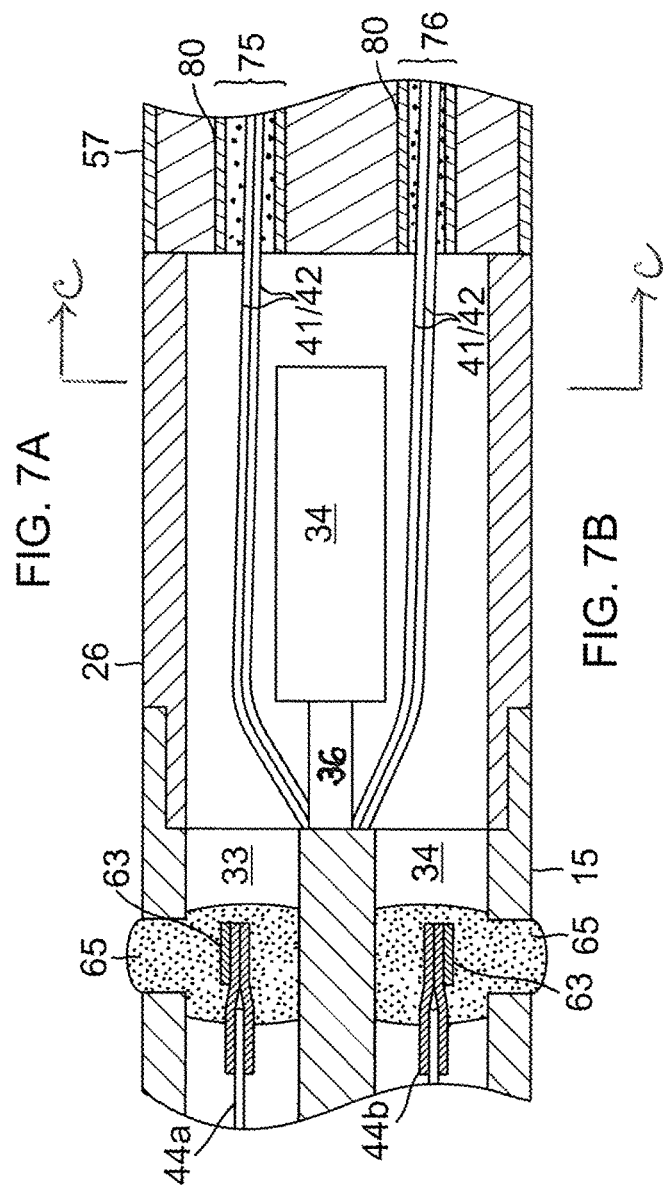
FIG. 7A
FIG. 7B

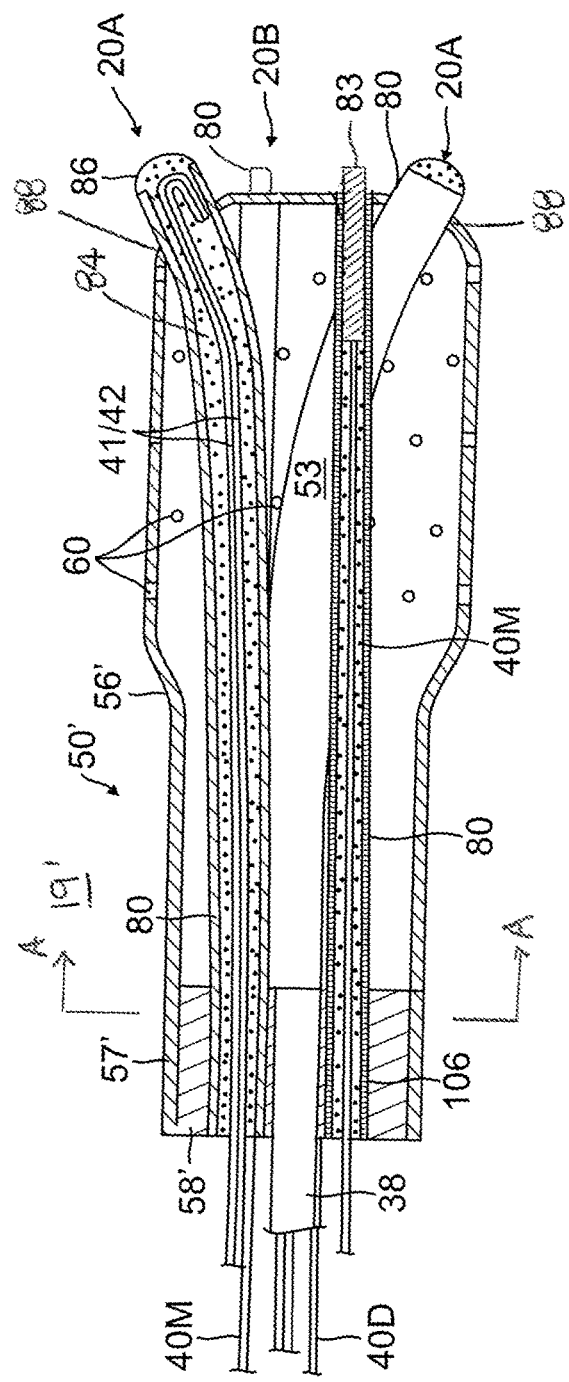
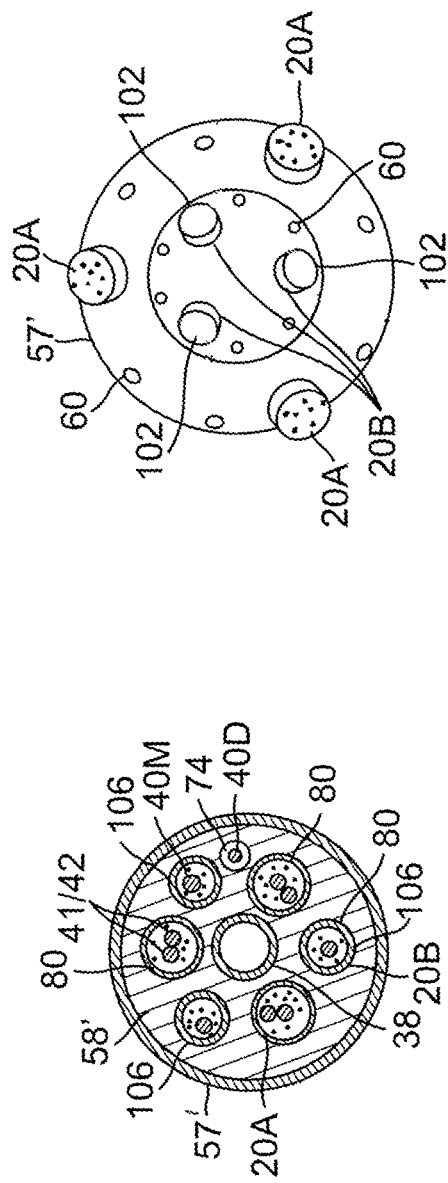
FIG. 9
FIG. 9A
FIG. 11

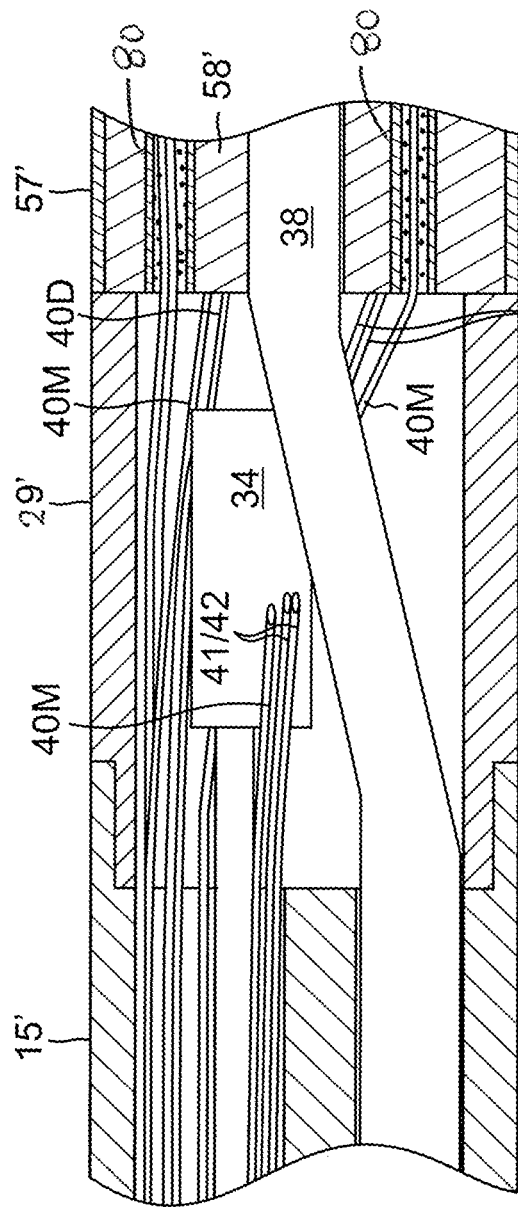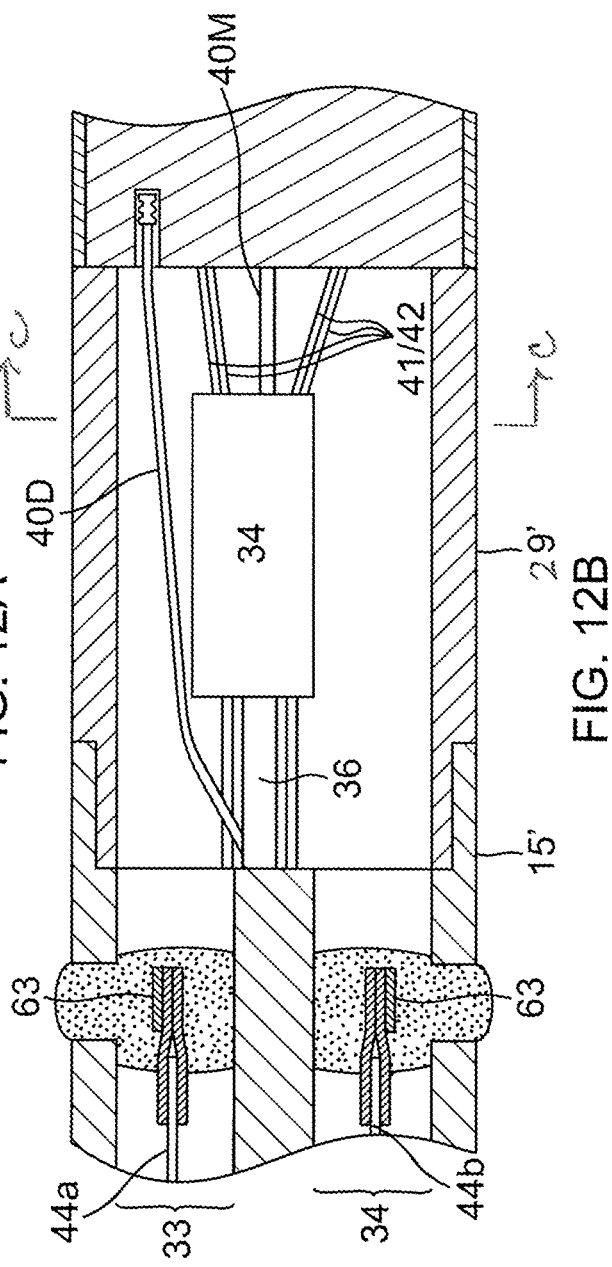
FIG. 12A
FIG. 12B

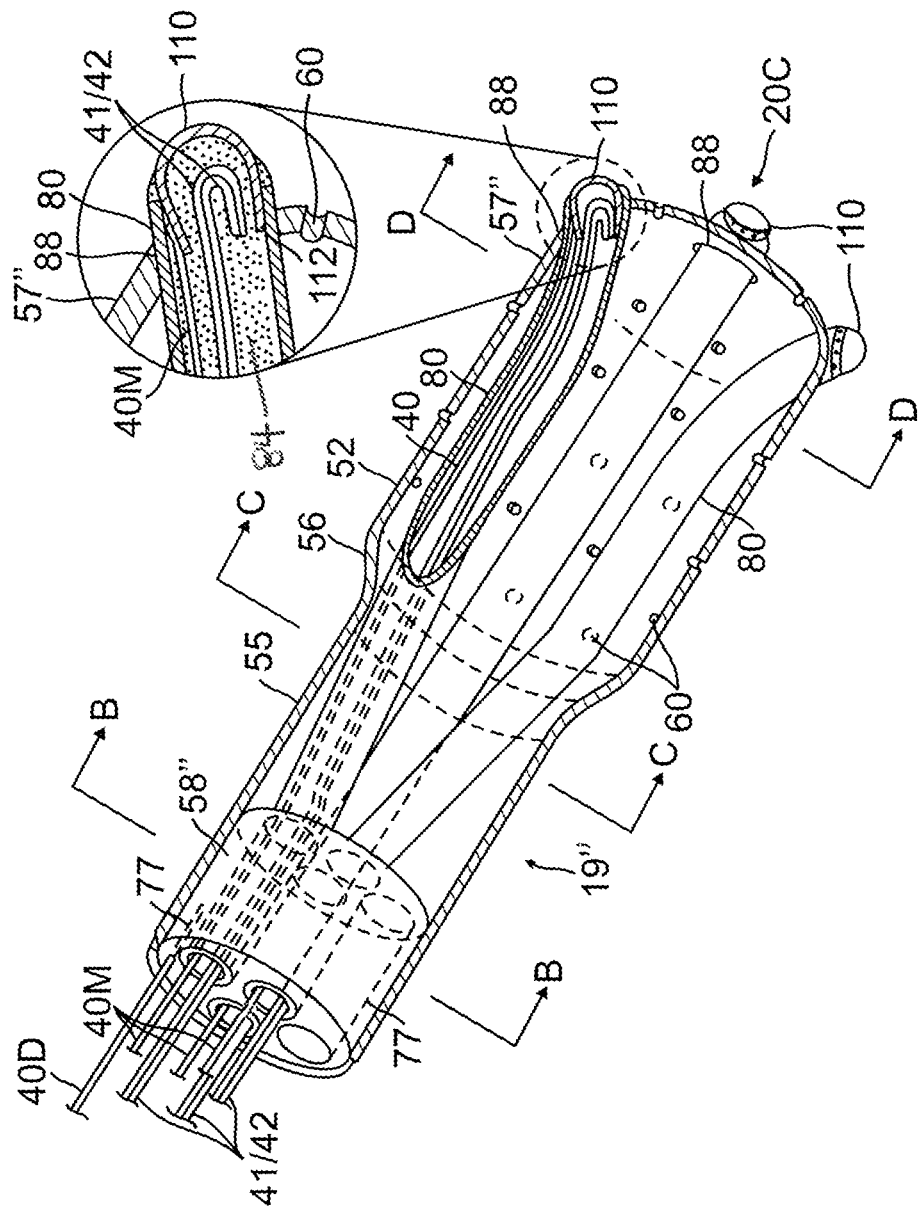

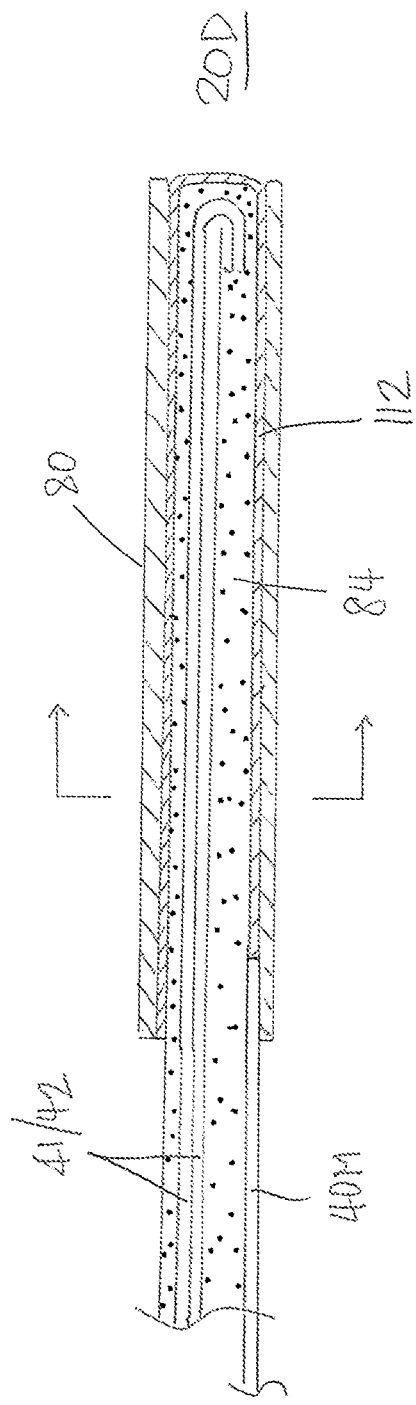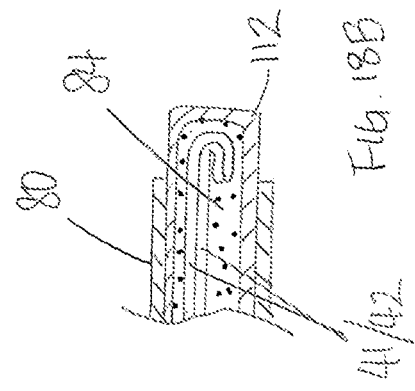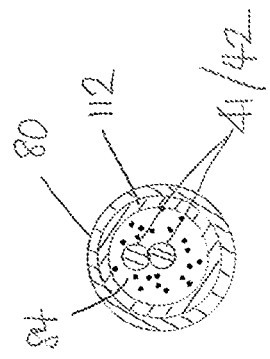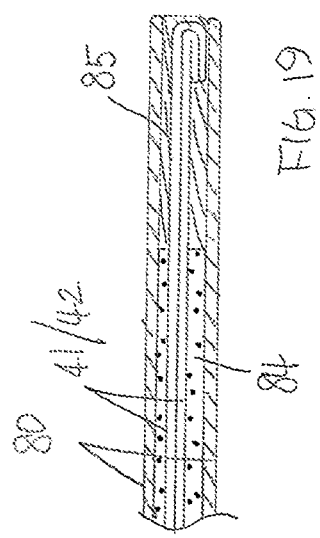

CATHETER ADAPTED FOR DIRECT TISSUE CONTACT

CROSS REFERENCE TO RELATED APPLICATION(S)

This application is a continuation of and claims priority to and the benefit of U.S. application Ser. No. 13/224,291 filed Sep. 1, 2011 now issued as U.S. Pat. No. 10,201,385, the entire content of which is incorporated herein by reference.

FIELD OF INVENTION

This invention relates generally to methods and devices for invasive medical treatment, and specifically to catheters, in particular, irrigated ablation catheters.

BACKGROUND

Ablation of myocardial tissue is well known as a treatment for cardiac arrhythmias. In radio-frequency (RF) ablation, for example, a catheter is inserted into the heart and brought into contact with tissue at a target location. RF energy is then applied through electrodes on the catheter in order to create a lesion for the purpose of breaking arrhythmogenic current paths in the tissue.

Irrigated catheters are now commonly used in ablation procedures. Irrigation provides many benefits including cooling of the electrode and tissue which prevents overheating of tissue that can otherwise cause the formation of char and coagulum and even steam pops. However, because tissue temperature is assessed during an ablation procedure to avoid such adverse occurrences, it is important that the temperature sensed accurately reflects the real temperature of the tissue and not merely the surface temperature of the tissue which can be biased by the cooling irrigation fluid from the catheter. Moreover, deeper tissue contact in general provides more accurate thermal and electrical readings, including improved impedance measurements for purposes including a determination of lesion size.

Accordingly, there is a desire for an irrigated ablation catheter with a distal end that can better probe tissue without significantly damaging or breaching the tissue, for more accurate measurements, including temperature sensing and impedance measurements.

SUMMARY OF THE INVENTION

The present invention is directed to an irrigated ablation catheter adapted for direct tissue contact by means of micro-elements (or micro-sensing members) that provide more accurate sensing of tissue, including thermal and electrical properties for temperature and impedance measurements.

In one embodiment, the catheter has an elongated body and a distal electrode assembly that has an electrode having a shell configured with an inner fluid chamber. The shell has a wall with at least one aperture formed on the distal portion of the shell which receives a distal end of a micro-element extending through the inner chamber. The distal end of the micro-element extends to at least through the aperture, if not also outside of the outer surface of the wall such that there is an exposed portion adapted to probe the tissue being ablated.

In a more detailed embodiment, the micro-element can be configured as a micro-temperature sensor or a micro-electrode, or a micro-element with both capabilities and functions. The micro-element has a guide tube adapted to protect the components in its central lumen against exposure to fluid and trauma, but is sufficiently flexible to adapt to the complex and small confines inside a hollow electrode that is adapted to receive irrigation fluid and pass the fluid outside of the electrode through irrigation apertures. For temperature sensing function, the micro-element includes a pair of temperature sensing wires (e.g., thermistor wires) encased in a suitable sealant. For electrical sensing function, including impedance sensing, the micro-element carries a micro-electrode member configured for direct tissue contact, and a lead wire. For both temperature sensing and electrical sensing functions, the dual-functioning micro-element carries a pair of thermistor wires, a micro-electrode member and a lead wire. The micro-electrode member can be a discrete structure from the thermistor wires, or an electrically-conductive coating applied to the wires.

In a more detailed embodiment, the distal electrode assembly include a plurality of micro-elements whose distal ends are arranged in a radial pattern along a circumference of the distal portion of the shell electrode. Exposed distal ends of the micro-elements extend at an angle relative to the longitudinal axis of the shell electrode. The angle may have at least a distal component, if not also a radial component, as a distal end of a catheter often does not approach and make tissue contact with a direct "on-axis" approach.

Also, the plurality of micro-electrodes can include one group of micro-thermistors and another group of micro-electrodes, each group being arranged on the same circumference at the distal end of the shell electrode, interspersed with each other, or on a larger circumference and a smaller circumference, respectively.

Furthermore, the exposed portion of a micro-element can range between about 0.2 mm and 1.0 mm, preferably between about 0.3 mm and 0.6 mm, and more preferably about 0.5 mm. Each micro-element may have a diameter ranging between about 0.01 inch to 0.03 inch, preferably about 0.0135 inch.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 2 is a perspective view of an electrode assembly in accordance with an embodiment of the present invention.

FIG. 2A is a perspective view of an electrode assembly in accordance with another embodiment of the present invention.

FIG. 3. is a side elevational view of the electrode assembly of FIG. 2 in direct contact with tissue.

FIG. 7A is a side cross-sectional view of a portion of the catheter of FIG. 1, including a connecting portion, taken along one diameter.

FIG. 7B is a side cross-sectional view of the portion of the catheter of FIG. 7A, taken along another diameter.

FIG. 9 is a side-cross-sectional view of the electrode assembly of FIG. 8.

FIG. 9A is an end cross-sectional view of the electrode assembly of FIG. 9, taken along line A-A.

FIG. 11 is an end view of the electrode assembly of FIG. 8.

FIG. 12A is a side cross-sectional view of an embodiment of a connection portion and an intermediate deflectable section suitable for the electrode assembly of FIG. 8, taken along one diameter.

FIG. 12B is a side cross-sectional view of an embodiment of a connection portion and an intermediate deflectable section suitable for the electrode assembly of FIG. 8, taken along another diameter.

FIG. 15 is a side cross-sectional view of the electrode assembly of FIG. 14.

FIG. 15A is an enlarged view of a distal end of a micro-element of FIG. 15.

FIG. 18 is a side cross-sectional view of a micro-element in accordance with an embodiment of the present invention.

FIG. 18A is an end cross-sectional view of the micro-element of FIG. 18, taken along line A-A.

FIG. 18B is a side cross-sectional view of a micro-element in accordance with another embodiment of the present invention.

FIG. 19 is a side cross-sectional view of a micro-thermistor in accordance with another embodiment of the present invention.

DETAILED DESCRIPTION OF THE INVENTION

Figure 1:
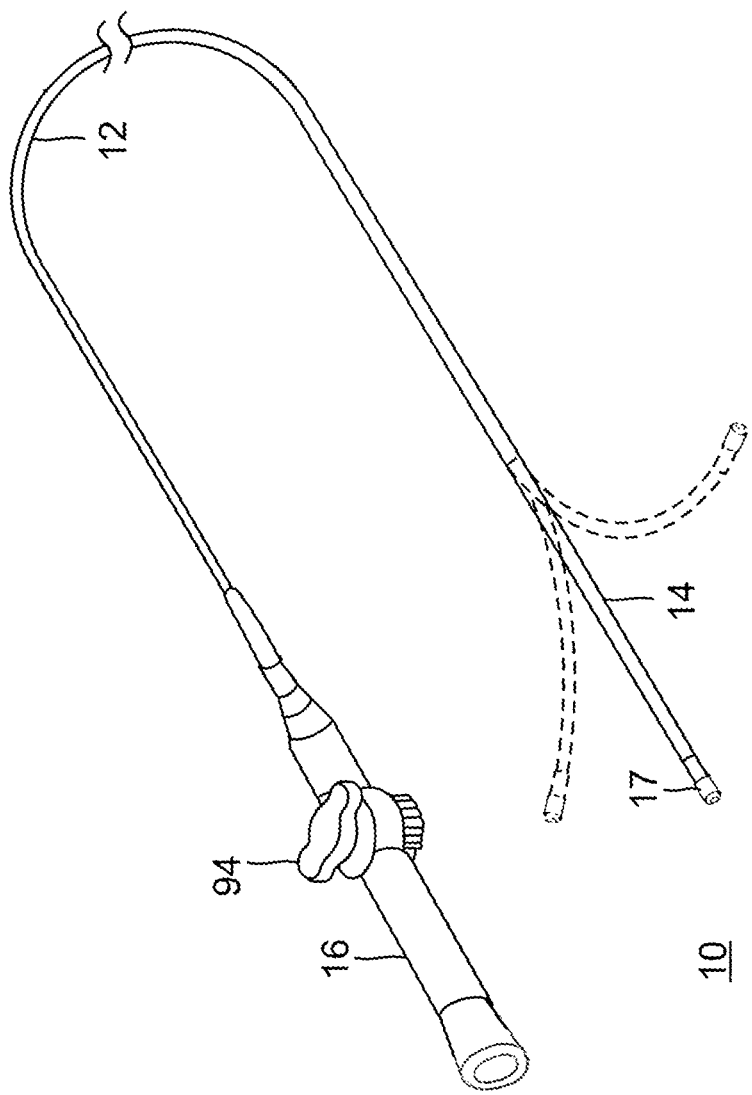
FIG. 1 is a perspective view of a catheter in accordance with an embodiment of the present invention.

As illustrated in FIGS. 1, 2 and 3, the present invention includes a steerable catheter 10 with a distal tip section 17 that includes an electrode assembly 19 and at least one micro-element 20 having an atraumatic distal end adapted for direct contact with target tissue 22. As illustrated in FIGS. 2 and 3, the distal end may have an external portion that is exposed and protrudes distally of the electrode assembly 19 to deform tissue and create micro-depression 24 where the external portion depresses and/or sinks into the micro-depression so as to be surrounded and buried in the tissue without penetrating, piercing or otherwise breaching the tissue. Alternatively, the distal end of the micro-element 20 may be flush with an outer surface of the electrode assembly 19, as illustrated in FIG. 2A. In either embodiment, each micro-element may be configured as a temperature sensor, e.g., thermistor, thermocouple, fluoroptic probe, and the like, or electrode for sensing and/or ablation. Each micro-element can also be configured to provide all aforementioned functions, as desired.

Referring to FIG. 1, the catheter 10 according to the disclosed embodiments comprises an elongated body that may include an insertion shaft or catheter body 12 having a longitudinal axis, and an intermediate section 14 distal of the catheter body that can be uni- or bi-directionally deflectable off-axis from the catheter body. Distal of the intermediate section 14 is the electrode assembly 19 carrying at least one micro-element. Proximal of the catheter body is a control handle 16 that allows an operator to maneuver the catheter, including deflection of the intermediate section 14.

Figure 4A:
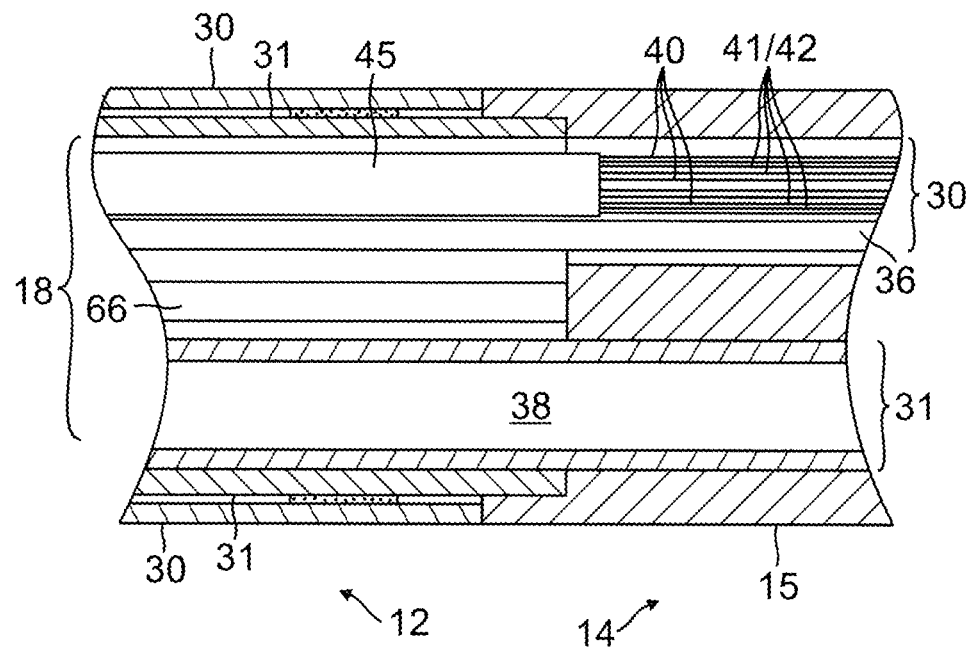
FIG. 4A is a side cross-sectional view of a portion of the catheter of FIG. 1, including a junction of a catheter body and an intermediate deflectable section, taken along one diameter.
Figure 4B:
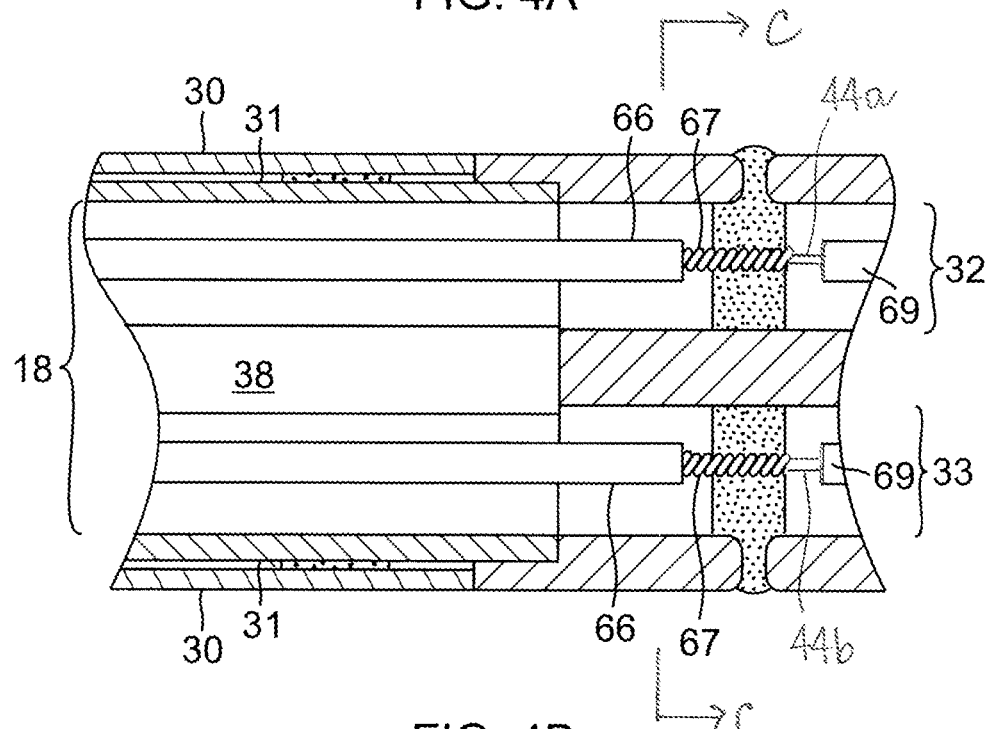
FIG. 4B is a side cross-sectional view of a portion of the catheter of FIG. 1, including a junction of a catheter body and an intermediate deflectable section, taken along another diameter.

In the depicted embodiment of FIGS. 4A and 4B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 30 made of polyurethane or PEBAX. The outer wall 30 comprises an imbedded braided mesh of stainless steel or the like, as is generally known in the art, to increase torsional stiffness of the catheter body 12 so that, when the control handle 16 is rotated, the intermediate section 14 and distal section 17 will rotate in a corresponding manner.

The outer diameter of the catheter body 12 is not critical, but is preferably no more than about 8 French, more preferably 7 French. Likewise the thickness of the outer wall 30 is not critical, but is thin enough so that the central lumen 18 can accommodate any desired wires, cables and/or tubes. The inner surface of the outer wall 30 is lined with a stiffening tube 31 to provide improved torsional stability. The outer diameter of the stiffening tube 31 is about the same as or slightly smaller than the inner diameter of the outer wall 30. The stiffening tube 31 can be made of any suitable material, such as polyimide, which provides very good stiffness and does not soften at body temperature.

Figure 4C:
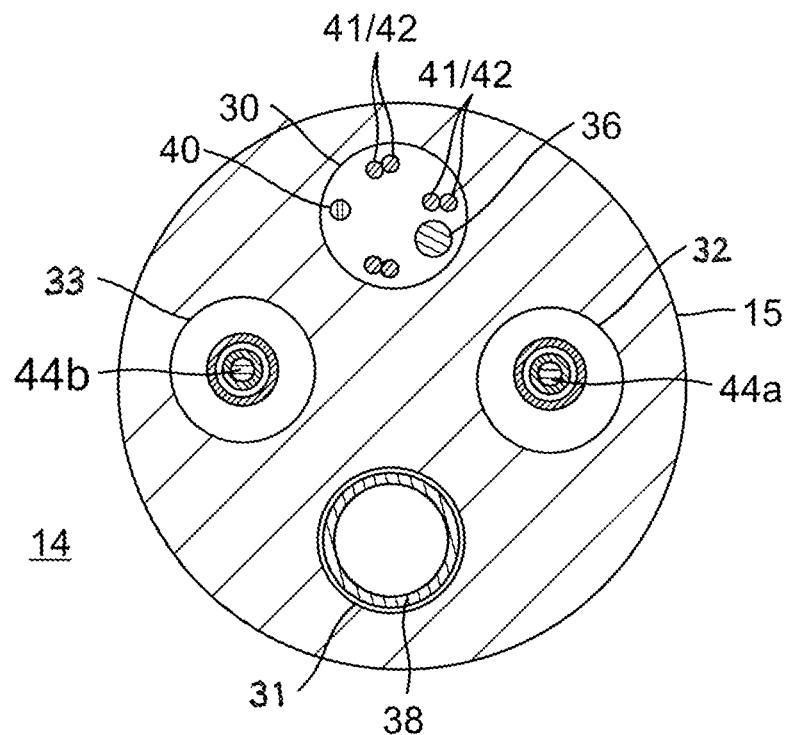
FIG. 4C is an end cross-sectional view of the portion of the catheter of FIG. 4B, taken along line C-C.

As illustrated in FIGS. 4A, 4B and 4C, the deflectable intermediate section 14 comprises a short section of tubing 15 having multiple lumens, each occupied by the various components extending through the intermediate section. In the illustrated embodiment, there are four lumens 30, 31, 32 and 33 as best seen in FIG. 4C. Passing through a first lumen 30 are lead wire 40 for the electrode assembly 19, a thermocouple pair 41/42 for each micro-element adapted as a thermistor, and a cable 36 for an electromagnetic position sensor 34. Passing through a second lumen 31 is a fluid irrigation tubing 38 to supply fluid to the electrode assembly 19. For at least uni-directional deflection, a first puller wire 44a passes through a third, off-axis lumen 32. For bi-directional deflection, a second puller wire 44b passes through a fourth, off-axis lumen 33.

The multi-lumened tubing 15 of the intermediate section 14 is made of a suitable non-toxic material that is preferably more flexible than the catheter body 12. A suitable material is braided polyurethane or PEBAX, i.e., polyurethane or PEBAX with an embedded mesh of braided stainless steel or the like. The plurality and size of each lumen are not critical, provided there is sufficient room to house the components extending therethrough. Position of each lumen is also not critical, except the positions of the lumens 32, 33 for the puller wires 44a, 44b. The lumens 32, 33 should be off-axis, and diametrically opposite of each other for bi-directional deflection along a plane.

The useful length of the catheter, i.e., that portion that can be inserted into the body can vary as desired. Preferably the useful length ranges from about 110 cm to about 120 cm. The length of the intermediate section 14 is a relatively small portion of the useful length, and preferably ranges from about 3.5 cm to about 10 cm, more preferably from about 5 cm to about 6.5 cm.

A preferred means for attaching the catheter body 12 to the intermediate section 14 is illustrated in FIGS. 4A and 4B. The proximal end of the intermediate section 14 comprises an inner circumferential notch that receives the outer surface of the distal end of the stiffening tube 31 of the catheter body 12. The intermediate section 14 and catheter body 12 are attached by glue or the like, for example, polyurethane. If desired, a spacer (not shown) can be provided within the catheter body 12 between the distal end of the stiffening tube 31 and the proximal end of the intermediate section 14 to provide a transition in flexibility at the junction of the catheter body 12 and the intermediate section, which allows the junction to bend smoothly without folding or kinking. An example of such a spacer is described in more detail in U.S. Pat. No. 5,964,757, the disclosure of which is incorporated herein by reference.

Figure 5:
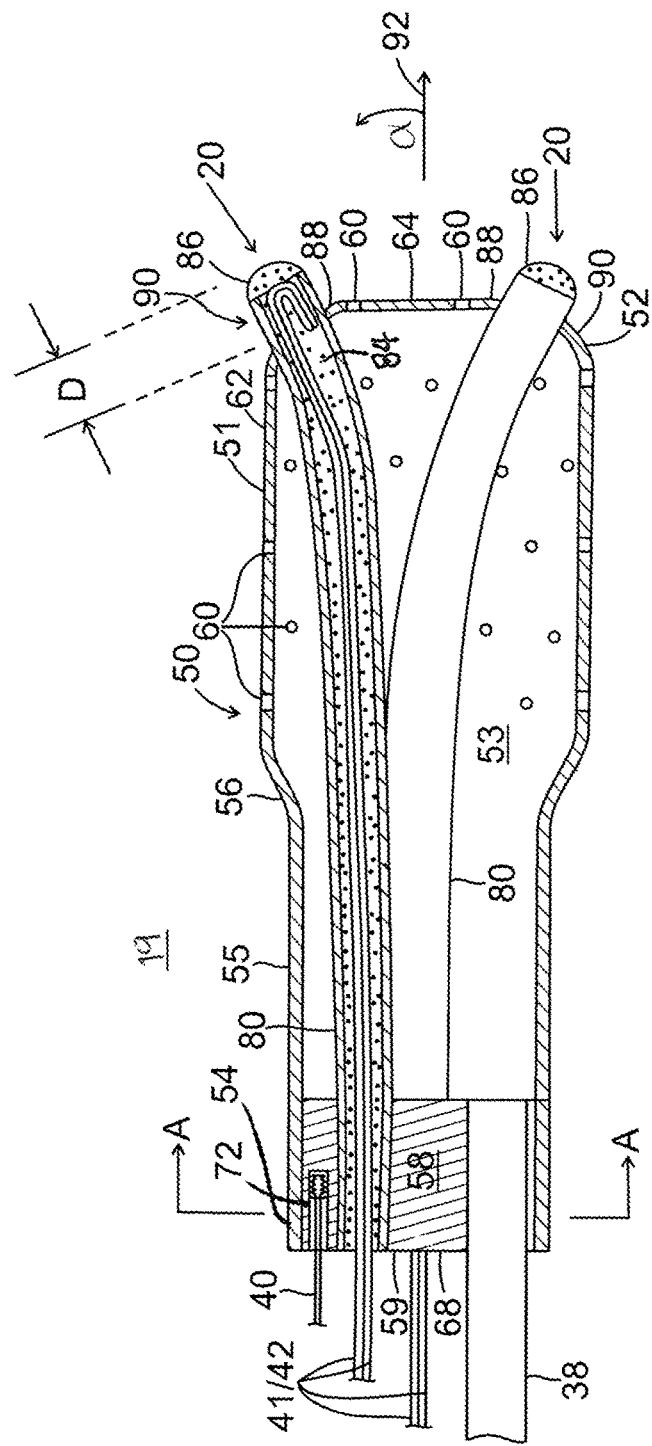
FIG. 5 is a side-cross-sectional view of the electrode assembly of FIG. 2.
Figure 5A:
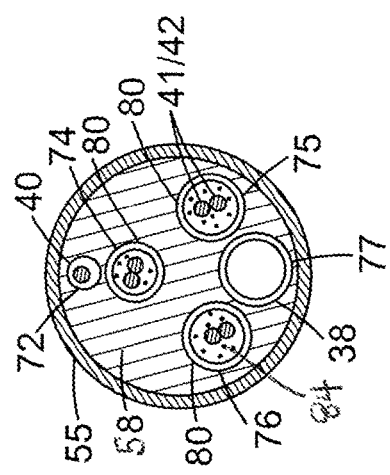
FIG. 5A is an end-cross-sectional view of the electrode assembly of FIG. 5, taken along line A-A.

With reference to FIGS. 5 and 5A, distal the intermediate section 14 is the distal electrode assembly 19 which includes an elongated, generally cylindrical, dome electrode 50 has a thin shell 57 and a plug 58. The shell 57 has an enlarged distal portion 51 with an atraumatic dome-shaped distal end 52. The distal portion defines a cavity or fluid chamber 53 that is in communication with an opening 54 at proximal end 55. Both the distal portion 52 and the proximal portion 55 have a circular cross-section although the diameter of the proximal portion may be slightly lesser than the diameter of the distal portion, and thus, there may be a transitional section 56 in between, forming a "neck". The shell 57 provides irrigation apertures 60 through which fluid entering and filling the chamber 53 can exit to outside of the dome electrode 50. In one embodiment, there are 56 irrigation apertures in total, with a greater portion of the apertures formed in radial wall 62, arranged in offset rows, and a lesser portion of the apertures formed in distal wall 64.

The plug 58 is shaped and sized to fit in and provide a fluid-tight seal of the opening 54 of the shell 57. In the illustrated embodiment, the plug is disc-shaped. Formed in the proximal face of the plug is a blind hole 72 receiving a lead wire 40D for the dome electrode 50. The plug also has a plurality of through-holes to allow passage of components and the like into the fluid chamber 53. In the illustrated embodiment, the plug has four through-holes 74, 75, 76, 77. Passing through each of through-holes 74, 75, 76 is a pair of thermistor wires 41/42. Received in through-hole 77 is the distal end of the irrigation tubing 38 allowing fluid delivered through the tubing 38 to enter the chamber 53. The plug and shell made be made of any suitable electrically-conductive material, such as palladium, platinum, iridium and combinations and alloys thereof, including, Pd/Pt (e.g., 80% Palladium/20% Platinum) and Pt/Ir (e.g., 90% Platinum/10% Iridium).

Advantageously, the wires 41/42 are sealed, insulated and protected by a routing guide tube 80 that extends from a proximal face 59 of the plug 58 to a short distance distal or beyond an outer surface of the distal wall 64 of the dome electrode 50. The guide tube may be made of any suitable material that is fluid-tight, electrically-nonconductive, thermally-insulating, and sufficiently flexible, e.g., polyimide, to form a thin-walled tubing. Accordingly, the wires are protected from corrosive exposure to the fluid entering the chamber 53 and electrically-insulated from the shell 57. The guide tube offers many advantages including (i) routing components through the hollow dome electrode having a complex curvature, (ii) protecting the components through the hollow dome electrode, and (iii) insulating the components to minimize cooling effects of fluid flowing through chamber.

The portion of the wires 41/42 extending through the guide tube 80 is potted along the length of the guide tube by a suitable material 84, e.g., polyurethane or epoxy, which is shaped to form an atraumatic distal end 86. The material should be corrosive fluid resistant, and be able to provide structural support and prevent large thermal gradients within the guide tubes that may otherwise result from exposure to irrigation fluid in the chamber 53. No air exists in the guide tube. It is understood that a suitable micro-thermistor may also be constructed using a pre-existing thermistor. As illustrated in FIG. 19, a pre-existing thermistor (including wires 41/42 previously encased in potting material 85) is inserted in guide tube 80 and sealed at the proximal portion with material 84.

As shown in FIG. 3, the distal end 86 and most, if not all, of the exposed distal portion of the micro-element 20 come in direct contact with the tissue 22 by forming a micro-depression 24 in the tissue and nesting therein so that at least the distal end if not also the exposed portion of the micro-element 20 is buried, enveloped, encapsulated and/or surrounded by tissue. Such direct contact with and probing of the tissue enables more accurate sensing.

The distal portion of each guide tube 80 extends through an aperture 88 formed in the shell 57 of the dome electrode 50. In the illustrated embodiment, the apertures 88 are generally aligned with the through-holes in the plug 58 and they are formed along the circumferential corner 90 of the dome electrode 50 generally between the radial wall 62 and the distal wall 64 so that the guide tube 80 extends at an angle α of about 45 degrees relative to a longitudinal axis 92 of the dome electrode. The guide tubes can be held in position by adhesive or can sit naturally if designed with a slight interference fit with the apertures 88. As such, there can be both a distal component and a radial component in the orientation of protrusion of the exposed distal portion of the micro-element 20. It is understood however that the location and/or angle α may vary as desired. In typical applications, the distal component is greater than the radial component for improved and direct contact with tissue.

Figure 6:
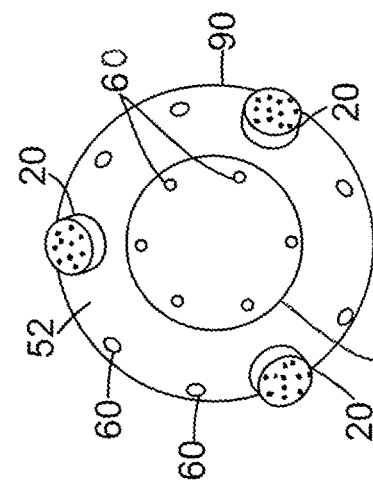
FIG. 6 is an end view of the electrode assembly of FIG. 2.

In one embodiment, the exposed portion of the micro-elements extending outside of the shell has a length D ranging between about 0.2 mm and 1.0 mm, preferably between about 0.3 mm and 0.6 mm, and more preferably about 0.5 mm. Each micro-element may have a diameter ranging between about 0.01 inch to 0.03 inch, preferably about 0.0135 inch. Although the illustrated embodiment has three micro-elements, with their distal ends arranged equidistance from each other in a radial pattern, at about 0 degrees, 120 degrees and 240 degrees about the longitudinal axis of the dome electrode (FIG. 6), it is understood that the plurality of micro-elements may vary, ranging between about two and six, and the angular position of the micro-elements may vary as well.

Figure 7C:
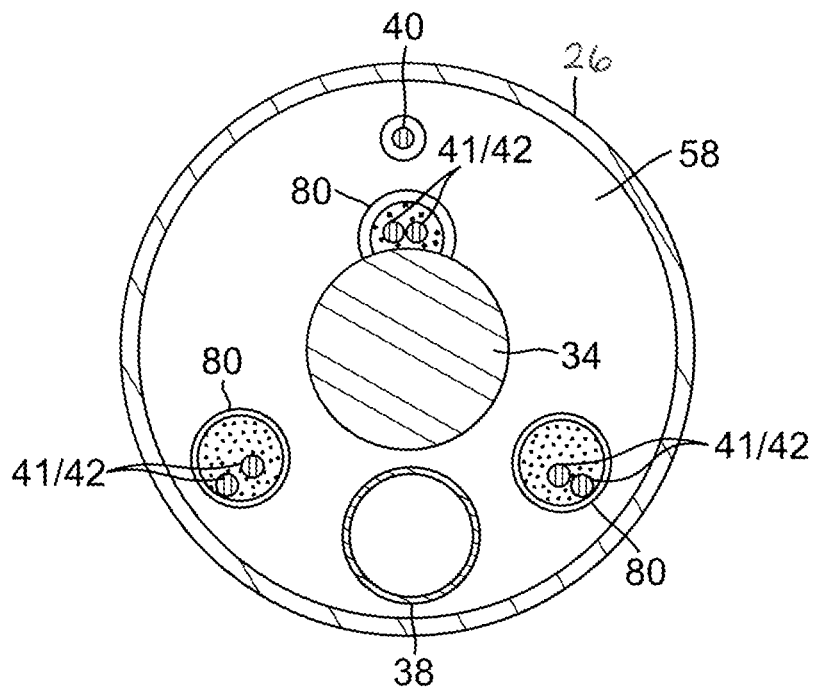
FIG. 7C is a distal end cross-sectional view of the portion of FIG. 7B, taken along line C-C.

With reference to FIGS. 7A, 7B and 7C, extending between the distal end of the intermediate section 14 and the dome electrode 50 is a connection portion 29 comprising a tubing 26. The tubing can be single-lumened and be made of any biocompatible plastic such as PEEK. The tubing provides space so that the components extending between the intermediate portion 14 and the dome electrode 50 to be reoriented as needed. Moreover, the position sensor 34 is housed within the tubing 26.

All of the wires pass through a common nonconductive protective sheath 45 (FIG. 4A), which can be made of any suitable material, e.g., polyimide, in surrounding relationship therewith. The sheath 45 extends from the control handle 16, through the catheter body 12 and to the intermediate section 14.

The pair of deflection puller wire 44a, 44b are provided for deflection of the intermediate shaft 14. The puller wires 44a, 44b extend through the central lumen 18 of the catheter body 12 and each through a respective one of the lumens 32 and 33 of the intermediate section 14. They are anchored at their proximal ends in the control handle 16, and at their distal end to a location at or near the distal end of the intermediate section 14 by means of T-bars 63 (FIG. 7B) that are affixed to the sidewall of the tubing 15 by suitable material 65, e.g., polyurethane, as generally described in U.S. Pat. No. 6,371,955, the entire disclosure of which is incorporated herein by reference. The puller wires are made of any suitable metal, such as stainless steel or Nitinol, and is preferably coated with Teflon® or the like. The coating imparts lubricity to the puller wire. For example, each puller wire has a diameter ranging from about 0.006 to about 0.010 inch.

As seen in FIG. 4B, each puller wire has a respective compression coil 64 in surrounding relation thereto. Each compression coil 67 extends from the proximal end of the catheter body 12 to at or near the proximal end of the intermediate section 14 to enable deflection. The compression coils are made of any suitable metal, preferably stainless steel, and are each tightly wound on itself to provide flexibility, i.e., bending, but to resist compression. The inner diameter of the compression coils is preferably slightly larger than the diameter of a puller wire. The Teflon® coating on the puller wire allows it to slide freely within the compression coil. Within the catheter body 12, the outer surface of the compression coil is covered by a flexible, nonconductive sheath 66, e.g., made of polyimide tubing. The compression coils are anchored at their proximal ends to the outer wall 30 of the catheter body 12 by proximal glue joints and to the intermediate section 14 by distal glue joints.

Within the lumens 32 and 33 of the intermediate section 14, the puller wires 44a, 44b extend through a plastic, preferably Teflon®, puller wire sheath 69 (FIG. 4B), which prevents the puller wires from cutting into the wall of the tubing 15 of the intermediate section 14 when the intermediate section 14 is deflected.

Longitudinal movement of the puller wires 44a, 44b relative to the catheter body 12 for bi-directional deflection is accomplished by appropriate manipulation of the control handle 16. A deflection knob 94 (FIG. 1) is provided on the handle which can be pivoted in a clockwise or counterclockwise direction for deflection in the same direction. Suitable control handles for manipulating more than one wire are described, for example, in U.S. Pat. Nos. 6,468,260, 6,500,167, and 6,522,933 and US Publication No. 2012/0143088, the entire disclosures of which are incorporated herein by reference.

The position sensor 48 can be a 3-coil electromagnetic sensor, or an assembly of single axis sensors ("SASs"). The position sensor enables the electrode assembly 19 (including the connection portion 29 housing the sensor) to be viewed under mapping systems manufactured and sold by Biosense Webster, Inc., including the CARTO, CARTO XP and NOGA mapping systems. Suitable SASs are described in U.S. Pat. No. 8,792,962, the entire disclosure of which is incorporated herein by reference.

With reference to FIGS. 8-13, an alternate embodiment of a catheter with a distal electrode assembly 19' is illustrated. Structural similarities exist between the embodiments disclosed herein. Accordingly, similar structures are identified by similar reference numerals.

Figure 8:
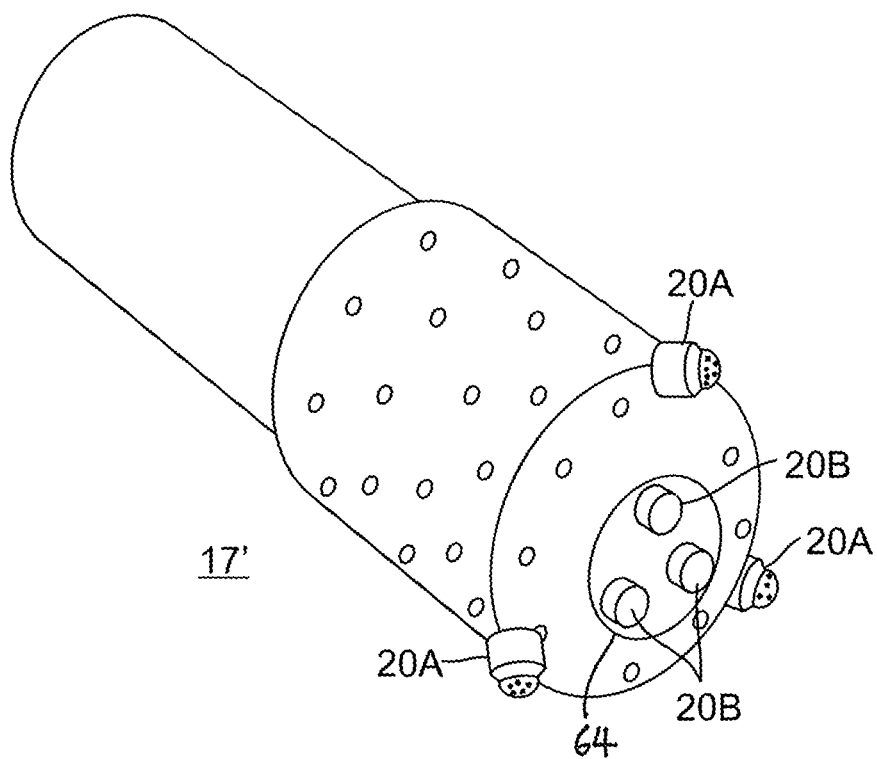
FIG. 8 is a perspective view of an electrode assembly in accordance with another embodiment of the present invention.
Figure 10:
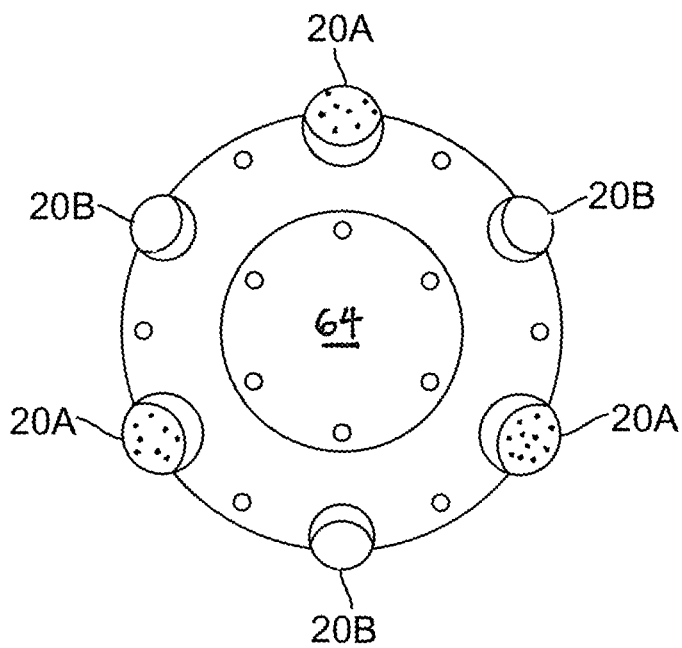
FIG. 10 is an end view of an electrode assembly in accordance with another alternate embodiment of the present invention.
Figure 12C:
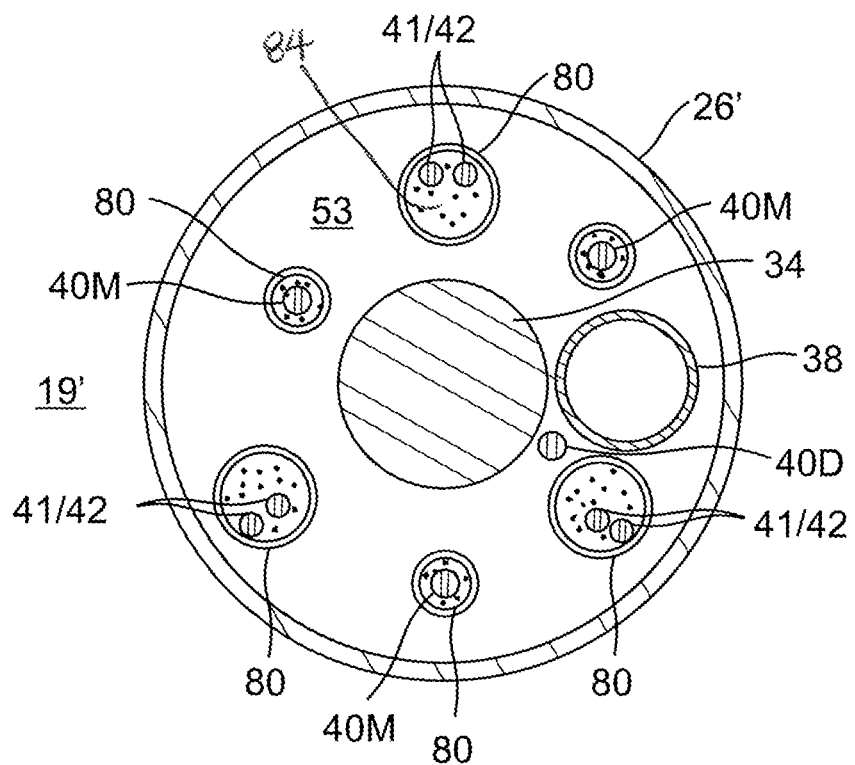
FIG. 12C is an end cross-sectional view of the connection portion of FIG. 12B, taken along line C-C.
Figure 13:
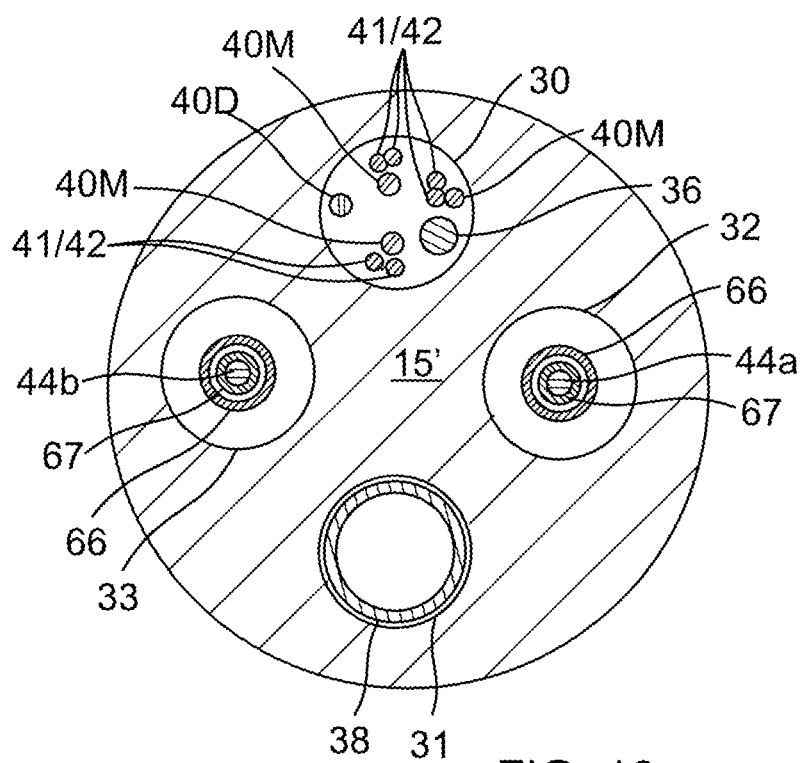
FIG. 13 is an end cross-sectional view of the intermediate deflectable section (near its proximal end) suitable for the electrode assembly of FIG. 8.

In the embodiment of FIGS. 8 and 9, a distal electrode assembly 19' has a first plurality of micro-elements 20A configured as thermistors, and a second plurality of micro-elements 20B configured as micro-electrodes, where each plurality may range between about two and six, and the first and second pluralities may be equal or unequal. In the illustrated embodiment, the first and second pluralities are equal, namely, three each, and the distal ends of micro-thermistor and the micro-electrodes can be interspersed along a common circumference on the distal wall (FIG. 10), or each occupy their own circumference on the distal wall (FIG. 11), with the micro-electrodes occupying an inner circumference and the micro-thermistors occupying an outer circumference. In either case, the distal ends of one group of micro-thermistors are arranged equi-distant from each other, in a radial pattern interspersed between each other, at about 0 degree, 120 degree and 240 degree about the longitudinal axis of the dome electrode, and the distal ends of the other group of micro-electrodes are arranged equi-distant from each other, in a radial pattern at about 60 degree, 180 degree and 300 degree.

Each micro-electrode has its respective guide tube 80 and lead wire 40M. In the illustrated embodiment, micro-electrode member 83 (FIG. 9) of the micro-electrode is a solid, elongated cylindrical member arranged in axial alignment with the dome electrode 50. The lead wire 40M is soldered at its distal end to the cylindrical member and extends through the lumen of the guide tube 80. The cylindrical member is exposed at a distal end 102 of guide tube 80 for direct with tissue. In one embodiment, the lead wire 40M is a copper wire. In one embodiment, the diameter of the micro-electrode 20B about 0.011 inch.

The distal ends 102 of the micro-electrodes 20B and the distal ends 86 of the micro-thermistors 20A come in direct contact with the tissue by forming micro-depressions in the tissue and nesting therein so that the distal ends are buried, enveloped, encapsulated and/or surrounded by tissue. Such direct and probing contact enables more accurate sensing by both the micro-electrodes and the micro-thermistors. However, as illustrated in the alternate embodiment of FIG. 2A, it is understood that the distal ends 102 and 86 may be flush with an outer surface of the shell of the dome electrode, so that the micro-electrodes 20A and 20B have no exposed portions or protrusions beyond the outer surface of the wall of the shell. The proximal ends of tubings 80 may also extend proximally of the proximal face of the plug 58, as desired or needed.

The plug 58' of the dome electrode 50 is configured with through-holes 106 for micro-electrode lead wires 40M with their guide tubes 80. Apertures 88 are provided in the shell 57' for these guide tubes 80. Again, position of the through-holes in the plug 58' is not critical. In the illustrated embodiment, the through-holes 106 are generally axially aligned with respective apertures 88 in the shell 57'.

With reference to FIGS. 12A, 12B, 12C and 13, proximal of the dome electrode 50' and the connection portion 29', the lead wires 40M (along with the thermistor wires 41/42, the position sensor cable 46 and the lead wire 40D for the dome electrode) extend through the first lumen 30 of the tubing 15 of the intermediate section 14, and through the central lumen 18 of the catheter body where they enter the control handle 16.

With reference to FIGS. 14-18, another alternate embodiment of a catheter with a distal electrode assembly 19" is illustrated. Structural similarities exist between the various embodiments disclosed herein. Accordingly, similar structures are identified by similar reference numerals.

Figure 14:
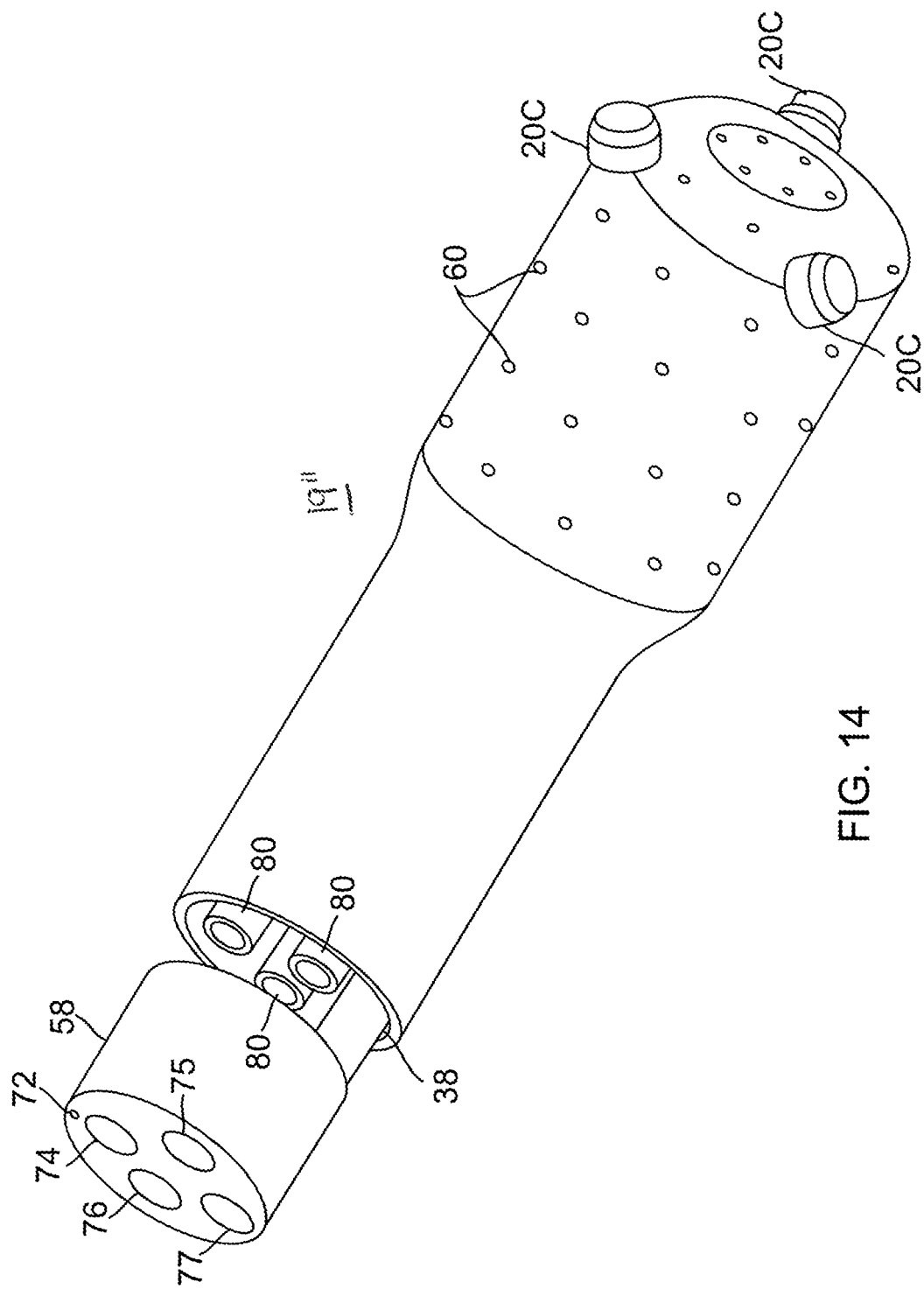
FIG. 14 is a partially exploded perspective view of an electrode assembly in accordance with yet another embodiment of the present invention.
Figure 15B:
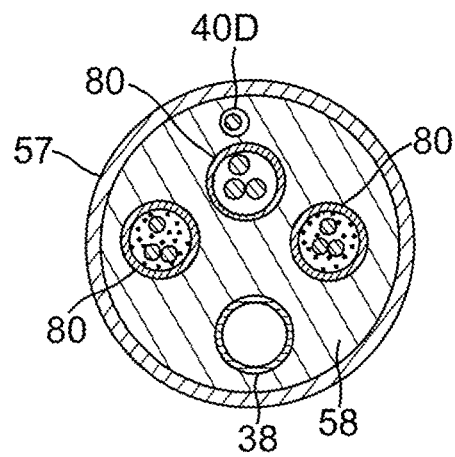
FIG. 15B is an end cross-sectional view of the electrode assembly of FIG. 15, taken along line B-B.
Figure 15C:
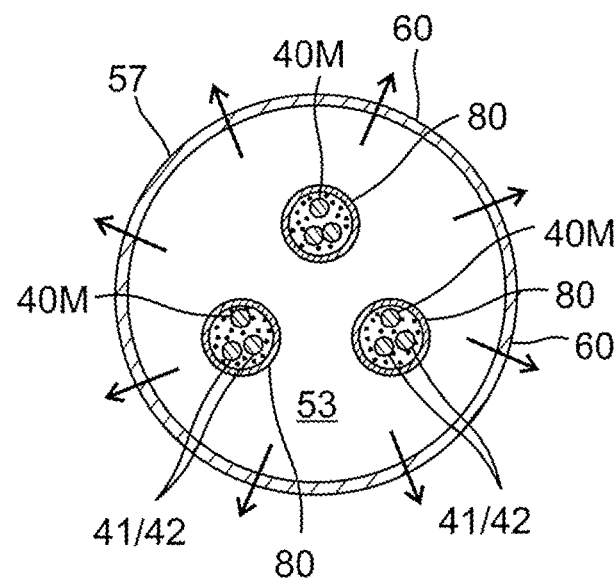
FIG. 15C is an end cross-sectional view of the electrode assembly of FIG. 15, taken along line C-C.
Figure 15D:
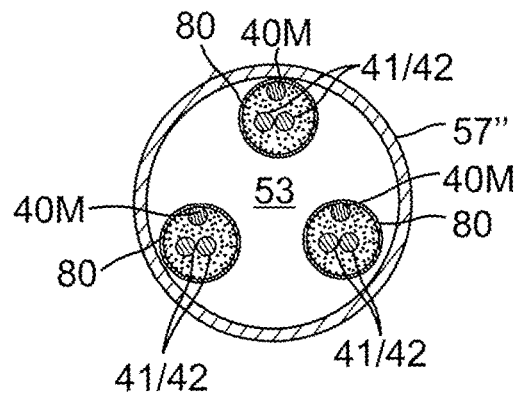
FIG. 15D is an end cross-sectional view of the electrode assembly of FIG. 15, taken along line D-D.
Figure 16A:
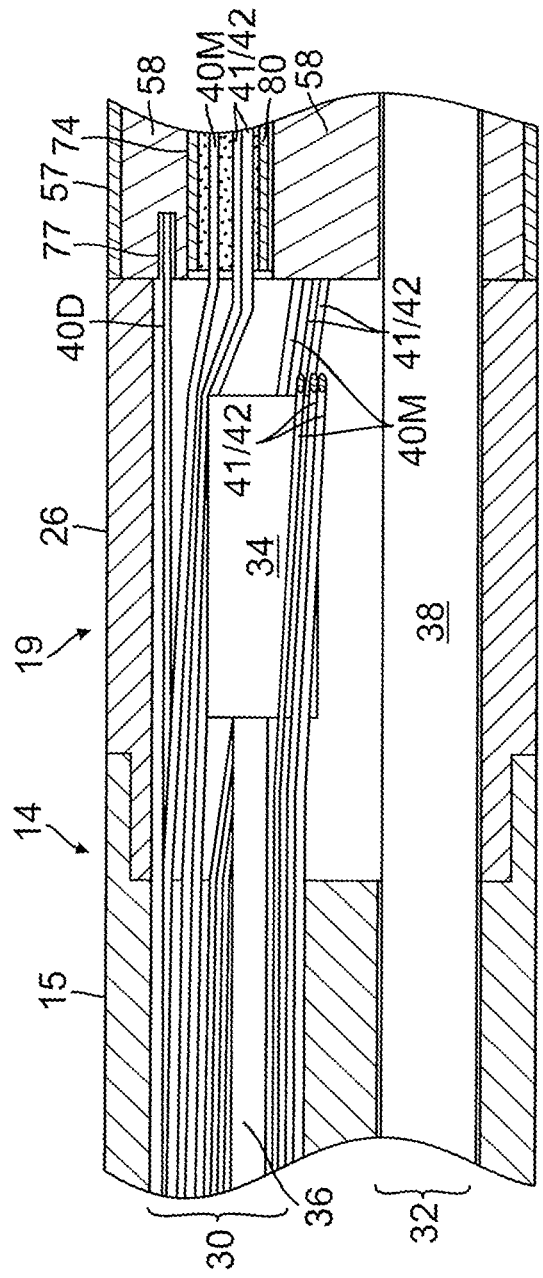
FIG. 16A is a side cross-sectional view of an embodiment of a connection portion and an intermediate deflectable section suitable for the electrode assembly of FIG. 15, taken along one diameter.
Figure 16B:
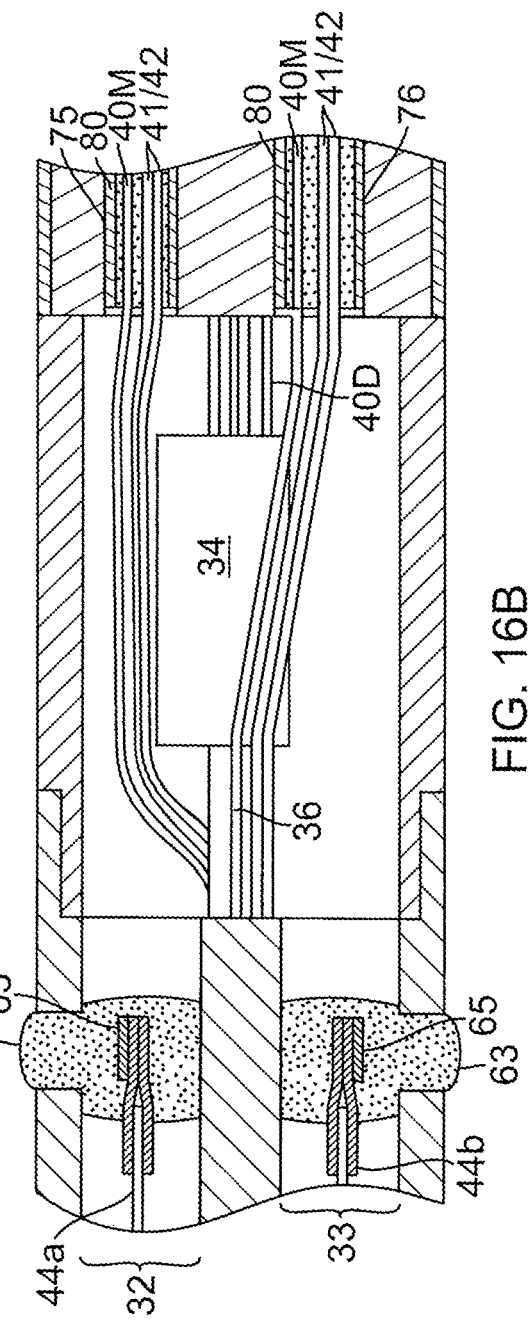
FIG. 16B is a side cross-sectional view of an embodiment of a connection portion and an intermediate deflectable section suitable for the electrode assembly of FIG. 15, taken along another diameter.
Figure 17A:
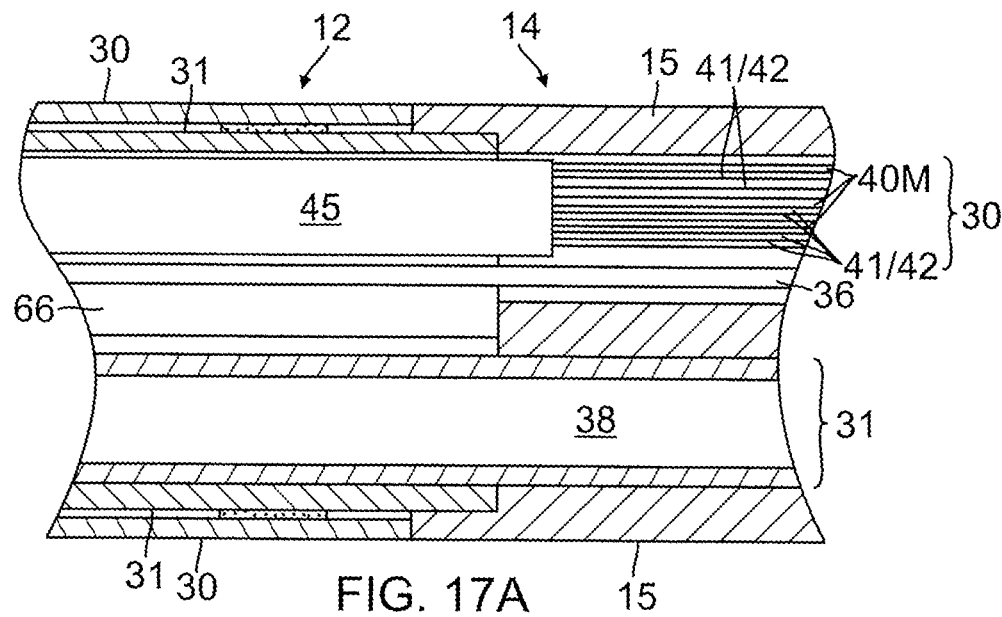
FIG. 17A is a side cross-sectional view of an embodiment of a junction between an intermediate deflectable section and a catheter body suitable for the electrode assembly of FIG. 15, taken along one diameter.
Figure 17B:
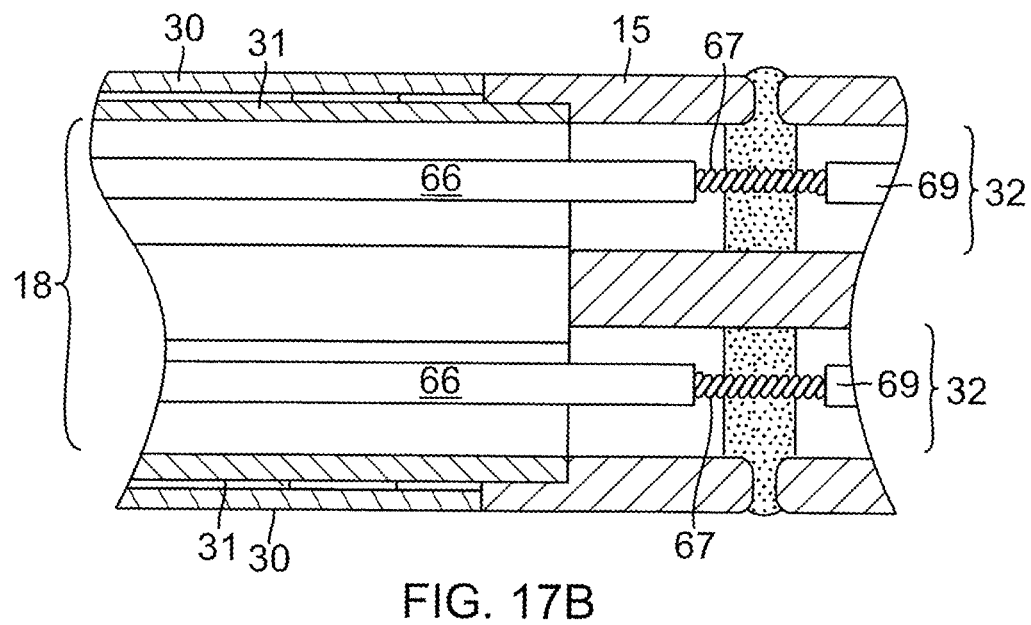
FIG. 17B is a side cross-sectional view of an embodiment of the junction between an intermediate deflectable section and a catheter body suitable for the electrode assembly of FIG. 15, taken along another diameter.

In the embodiment of FIGS. 14-16, the distal electrode assembly 19" has a plurality of micro-elements 20C, each configured to function both as a micro-thermistor and a micro-electrode within a single common guide tube. In the illustrated embodiment, the thermistor wires 41/42 extend through the guide tube 80 in a manner as previously described. The electrode member of the micro-element takes the form of a shell cap 110 is mounted on the distal ends of the thermistor wires 41/42. Best shown in FIG. 15A, the shell cap 110 is cup-shaped with a proximal cylindrical portion 112 defining an opening and a distal portion with a generally U-shaped cross-section. The shell cap can be made of any suitable electrically conductive material, for example, palladium, platinum, iridium and combinations and alloys thereof, including, Pd/Pt (e.g., 80% Palladium/20% Platinum) and Pt/Ir (e.g., 90% Platinum/10% Iridium). The shell cap can have a thickness ranging between about 0.005 inch and 0.001 inch, preferably about 0.002 inch. The length of the proximal portion can vary. The longer the length the more structural support is provided to the micro-element. The length can be about half the length of the shell. The opening of the shell cap sits inside the distal end of the guide tube such that an outer circumferential surface of the opening 112 of the cap interfaces an inner circumferential surface of the distal end of the guide tube 80. Soldered to a location on the outer or inner circumferential surface of the cap 110 is a distal end of the lead wire 40M which extends proximally through the lumen of the guide tube 80 along with the thermistor wires 41/42. The lead wire 40M and the thermistor wires 41/42 are isolated from each other by a suitable electrically nonconductive and non-thermally insulative material 84, e.g., polyurethane or epoxy, that fills the lumen of the guide tube 80. In the illustrated embodiment, there are three dual-function micro-electrodes 20C, with their distal ends arranged equi-distant from each other, in a radial pattern at about 0 degree, 120 degree and 240 degree about the longitudinal axis of the dome electrode. It is understood that the plurality and angular position may be varied as desired. The plurality may range between about two and six, preferably about three.

The distal end of each micro-element comes in direct contact with the tissue by forming a micro-depression in the tissue and nesting therein so that the distal end is buried, enveloped, encapsulated and/or surrounded by tissue. Such direct and probing contact enables more accurate electrical and thermal sensing.

The plug 58" is configured with through holes 74-76 for micro-elements 20C with their guide tubes 80, through-hole 77 for irrigation tubing 38, and blind-hole 72 for dome electrode lead wire 40D. Apertures 88 are provided in the shell 57" wall for the micro-elements 20C. Again, position of the through-holes is not critical. In the illustrated embodiment, the through holes 74-76 in the plug are generally axially aligned with respective apertures 88 in the shell.

With reference to FIGS. 16A, 16B, 17A and 17B, proximal the dome electrode 50" and the connection portion 29", the lead wires 40M (along with the thermistor wires 41/42, the position sensor cable 46 and the lead wire 40D for the dome electrode) extend through the first lumen 30 of the tubing 15 of the intermediate section 14, and through the central lumen 18 of the catheter body where they enter the control handle 16.

FIGS. 18 and 18A illustrate an alternate embodiment of a dual-function micro-element 20D. Thermistor wires 41/42 are encased in a suitable sealant 84, e.g., polyurethane or epoxy. The sealed wires are then coated with a coating 120 of electrically conductive material, e.g., gold impregnated epoxy, that serves as the micro-electrode member. Lead wire 40M is connected to the coating 120. The sealed and coated wires are further encased in a guide tube 80 to electrically isolate the wires and the coating from the dome electrode. Where the distal ends of micro-element protrudes beyond the outer surface of the wall of the shell, the distal end of the sealed and coated wires are exposed radially and distally (FIG. 18). Where the distal ends of micro-elements are flush with the outer surface of the wall of the shell, the distal end of guide tubes 80 is coextensive with the distal end of the sealed and coated wires, leaving only the distal face exposed (FIG. 18B).

All of the through-holes in the plug in each embodiment is sealed around the guide tubes with any suitable sealant or adhesive, for example, polyurethane to prevent fluid leakage. The adhesive is first applied to the distal face of the plug prior to being pressed into the shell. After the electrode assembly is constructed, adhesive is applied to the proximal face of the plug for additional confidence in no fluid leakage. Components extending through the guide tubes, including lead wires and thermistor wires, can be anchored proximally in the catheter, for example, in the intermediate section 14, to provide strain relief.

It is also understood that the distal ends of the micro-elements may be flush with the radial and distal walls of the shell. That is, while the aforementioned embodiments provide micro-elements with a distal end that protrudes from the shell, the present invention includes a distal electrode assembly wherein the distal ends of the micro-elements are coextensive with the outer surface of the shell and do not protrude beyond it. After the electrode assembly is constructed, any protruding distal ends of the micro-elements can be buffed away until the distal ends are even with the outer surface of the shell.

For the foregoing embodiments, the wire 41 of the wire pair is a copper wire, e.g. a number "40" copper wire and the wire 42 is a constantan wire. The wires of each pair are electrically isolated from each other except at their distal ends where they are twisted together. Moreover, lead wires 40D and 40M, thermistor wires 41/42, puller wires 44a and 44b, cable sensor 36 and irrigation tubing 38 extend proximally through the central lumen 18 of the catheter body 12 before entering the control handle where they are anchored or passed through to appropriate connectors or couplers inside the control handle or proximal thereof.

In operation, an operator, such as a cardiologist, inserts a guiding sheath through the vascular system of the patient so that the distal end of the guiding sheath enters a chamber of the patient's heart, for example, the left atrium. Operator then advances the catheter through the guiding sheath. The catheter is fed through the guiding sheath until at least the electrode assembly 19 is past the distal end of the guiding sheath.

The operator can advance and retract the catheter in the left atrium and deflect the intermediate portion 14 as appropriate to aim the electrode assembly 19 toward target tissue. The catheter is advanced until the distal end of the dome electrode contacts tissue. RF energy can be applied to the dome electrode to ablate the tissue for forming a lesion. Irrigation fluid is delivered via the irrigation tubing to the dome electrode where it enters the chamber and exits via the irrigation apertures for various purposes, including cool the dome electrode and keeping the surface free of char and coagulum. Additional normal force can be applied to so that the micro-elements depress the tissue and become nested in the tissue for direct contact which allows for more accurate sensing, including more accurate impedance measurement and more accurate temperature sensing. In the latter instance, deeper temperature sensing via the micro-elements provides a more accurate temperature reading of the tissue to avoid adverse effects of tissue overheating such as charring and steam pop, as opposed to merely the tissue surface temperature which can be biased by the cooling temperature of the irrigation fluid. Deeper impedance measurements are provides for more accurate measurements for various purposes including a determination of lesion size.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter, comprising:
    an elongated body;
    a distal electrode assembly, including:
        an electrode having a shell configured with an inner chamber, the shell having a wall defining a proximal portion and a distal portion, the wall of the distal portion having at least two apertures spaced apart from each other, and the inner chamber being configured to receive fluid;
        one or more electrode micro-elements and a plurality of temperature sensing micro-elements extending through the inner chamber between the proximal portion and the distal portion such that the one or more electrode micro-elements and the plurality of temperature sensing micro-elements extend through the fluid when the fluid is received in the inner chamber, each of the one or more electrode micro-elements and the plurality of temperature sensing micro-elements having a distal end fixedly received in a separate one of the at least two apertures of the wall of the distal portion, each of the one or more electrode micro-elements and the plurality of temperature sensing micro-elements is configured to directly contact tissue; and
    a control handle.

2. The catheter of claim 1, wherein the wall of the shell has a plurality of irrigation apertures configured to allow fluid received in the inner chamber to flow from inside the inner chamber to outside the inner chamber.

3. The catheter of claim 2, wherein the distal end of each of the one or more electrode micro-elements and the plurality of temperature sensing micro-elements includes an exposed portion outside of the wall of the shell.

4. The catheter of claim 3, wherein the exposed portion extends at an angle having a distal component and a radial component relative to the longitudinal axis of the electrode.

5. The catheter of claim 3, wherein the exposed portion has a length of about 0.2 mm to about 1.0 mm.

6. The catheter of claim 3, wherein the exposed portion has an atraumatic configuration configured to form a micro-depression in tissue without breaching the tissue.

7. The catheter of claim 1, wherein each of the one or more electrode micro-elements includes a tube with a distal end, a lumen and at least one wire extending through the lumen, the at least one wire having a distal end attached to a micro-electrode at the distal end of the respective electrode micro-element.

8. The catheter of claim 1, wherein each of the plurality of temperature sensing micro-elements has a tube with a distal end, a lumen and at least two wires extending through the lumen, the at least two wires being configured for temperature sensing.

9. The catheter of claim 1, wherein:
    the one or more electrode micro-elements comprises a plurality of electrode micro-elements, the distal ends of the electrode micro-elements being arranged in a radial pattern in the distal portion of the electrode about a longitudinal axis of the electrode; and/or
    the distal ends of the plurality of temperature sensing micro-elements are arranged in a radial pattern in the distal portion of the electrode about the longitudinal axis of the electrode.

10. The catheter of claim 9, wherein:
    the plurality of electrode micro-elements comprises two to six electrode micro-elements; and/or
    the plurality of temperature sensing micro-elements comprises two to six temperature sensing micro-elements.

11. The catheter of claim 9, wherein:
    the plurality of electrode micro-elements comprises three electrode micro-elements; and/or
    the plurality of temperature sensing micro-elements comprises three temperature sensing microelements.

12. The catheter of claim 9, wherein the plurality of temperature sensing micro-elements comprises three temperature sensing micro-elements arranged generally equi-distant from each other in a radial pattern about a longitudinal axis of the electrode.

13. The catheter of claim 12, wherein the distal ends of the three temperature sensing micro-elements are arranged generally at 0 degrees, 120 degrees and 240 degrees about the longitudinal axis of the electrode.

14. The catheter of claim 9, wherein the plurality of electrode micro-elements comprises three electrode micro-elements arranged generally equi-distant from each other in a radial pattern about a longitudinal axis of the electrode.

15. The catheter of claim 14, wherein the distal ends of the three electrode micro-elements are arranged generally at 60 degrees, 180 degrees and 300 degrees about the longitudinal axis of the electrode.

16. The catheter of claim 9, wherein:
the plurality of electrode micro-elements comprises six electrode micro-elements; and/or
the plurality of temperature sensing micro-elements comprises six temperature sensing micro-elements.

17. The catheter of claim 1, wherein the one or more electrode micro-elements comprises a plurality of electrode micro-elements configured for impedance sensing, and the plurality of temperature sensing micro-elements is configured for temperature sensing,
wherein each of the electrode micro-elements has a tube housing a micro-electrode and a lead wire; and
wherein each of the temperature sensing micro-elements has a tube housing a pair of wires configured for temperature sensing.

18. The catheter of claim 17, wherein distal ends of the electrode micro-elements are arranged in a radial pattern along a circumference of the distal portion of the shell about a longitudinal axis of the electrode.

19. The catheter of claim 18, wherein the distal ends of the temperature sensing micro-elements are also arranged in a radial pattern along the circumference, interspersed between the distal ends of the electrode micro-elements.

20. The catheter of claim 18, wherein the distal ends of the temperature sensing micro-elements are arranged in a radial pattern along a different circumference of the distal portion of the shell about the longitudinal axis of the electrode.

* * * * *